United States Patent
Perera et al.

(10) Patent No.: US 10,260,019 B2
(45) Date of Patent: Apr. 16, 2019

(54) HYDROXYAROMATIC SUCCINIMIDE DETERGENTS FOR LUBRICATING COMPOSITIONS

(71) Applicant: The Lubrizol Corporation, Wickliffe, OH (US)

(72) Inventors: Jayasooriya Sujith Perera, Twinsburg, OH (US); Gary M. Walker, Allestree (GB); Daniel J. Saccomando, Sheffield (GB); Nicolas Proust, Painesville, OH (US); Stephen J. Cook, Belper (GB)

(73) Assignee: The Lubrizol Corporation, Wickliffe, OH (US)

( * ) Notice: Subject to any disclaimer, the term of this patent is extended or adjusted under 35 U.S.C. 154(b) by 1 day.

(21) Appl. No.: 15/634,206

(22) Filed: Jun. 27, 2017

(65) Prior Publication Data

US 2018/0002630 A1 Jan. 4, 2018

Related U.S. Application Data

(60) Provisional application No. 62/356,762, filed on Jun. 30, 2016.

(51) Int. Cl.
| | |
|---|---|
| *C11D 1/66* | (2006.01) |
| *C10M 133/16* | (2006.01) |
| *C10M 133/44* | (2006.01) |
| *C10M 135/28* | (2006.01) |
| *C10M 139/00* | (2006.01) |
| *C10M 169/04* | (2006.01) |
| *C07D 207/404* | (2006.01) |

(52) U.S. Cl.
CPC ....... *C10M 133/44* (2013.01); *C07D 207/404* (2013.01); *C10M 133/16* (2013.01); *C10M 135/28* (2013.01); *C10M 139/00* (2013.01); *C10M 169/04* (2013.01); *C10M 2203/1025* (2013.01); *C10M 2207/027* (2013.01); *C10M 2215/086* (2013.01); *C10M 2215/28* (2013.01); *C10M 2215/30* (2013.01); *C10M 2219/046* (2013.01); *C10M 2219/087* (2013.01); *C10M 2219/09* (2013.01); *C10M 2227/06* (2013.01); *C10N 2230/04* (2013.01); *C10N 2240/10* (2013.01); *C10N 2240/102* (2013.01); *C11D 1/66* (2013.01)

(58) Field of Classification Search
CPC .............. C10M 133/16; C10M 133/44; C10M 133/56; C10M 135/28; C10M 139/00; C10M 169/04; C10M 2203/1025; C10M 2207/027; C10M 2215/086; C10M 2215/28; C10M 2215/30; C10M 2219/046; C10M 2219/087; C10M 2219/09; C10M 2227/06; C10N 2230/04; C10N 2240/10; C10N 2240/102; C07D 207/404; C11D 1/66

See application file for complete search history.

(56) References Cited

U.S. PATENT DOCUMENTS

| | | | |
|---|---|---|---|
| 4,354,950 A * | 10/1982 | Hammond | C07D 207/412 508/292 |
| 4,919,684 A | 4/1990 | Nalesnik et al. | |
| 5,241,003 A * | 8/1993 | Degonia | C07C 51/567 508/188 |
| 5,620,486 A * | 4/1997 | Cherpeck | C07D 207/412 44/347 |
| 5,633,326 A * | 5/1997 | Patil | C08F 271/00 525/327.6 |
| 2012/0247412 A1* | 10/2012 | Toman | C10M 133/08 123/1 A |

FOREIGN PATENT DOCUMENTS

| | | | | |
|---|---|---|---|---|
| GB | 1194286 A | * | 6/1970 | ......... C07D 207/412 |
| GB | 1194286 A | | 6/1970 | |
| JP | 2014172829 A | | 9/2014 | |
| WO | 2015-183685 A1 | | 12/2015 | |

OTHER PUBLICATIONS

"A Search for Ecofriendly Detergent/Dispersant Additives for Vegetable-Oil Based Lubricants", Journal of Surfactants and Detergents, Springer/OACS, USA, vol. 15, No. 4, 11 Dec. 2011, pp. 399-409.

* cited by examiner

*Primary Examiner* — James C Goloboy
(74) *Attorney, Agent, or Firm* — Michael Miller; Eryn Fuhrer; Teresan Gilbert

(57) ABSTRACT

A lubricating composition includes an oil of lubricating viscosity and an N-substituted hydroxyaromatic succinimide or a salt thereof.

19 Claims, No Drawings

HYDROXYAROMATIC SUCCINIMIDE DETERGENTS FOR LUBRICATING COMPOSITIONS

PRIORITY CLAIM

This application claims priority from U.S. Provisional Application 62/356,762 filed on Jun. 30, 2016, which is hereby incorporated by reference.

BACKGROUND

The exemplary embodiment relates to lubricant additives and in particular to succinimide derivatives of hydroxyaromatic compounds that are useful in lubricating compositions.

Thermal and mechanical stresses on lubricants, such as engine and driveline oils, tend to increase formation of deposits on the lubricated components, such as internal combustion engines and driveline components. This can negatively impact the performance of the lubricated components through reduction in engine efficiency or overall life-expectancy. Such lubricants generally incorporate, in addition to a base oil, a number of additives, including friction modifiers, antiwear agents, antioxidants, dispersants, and detergents, that are used to protect lubricated components from wear, oxidation, soot deposits, corrosion, acid build up, and the like, and to improve water tolerance and compatibility of formulation components.

Branched para-$C_{12}$-alkylphenols, including p-dodecyl-phenol (PDDP), formed from tetrapropene, have seen extensive commercial use as chemical intermediates in the production of oil and lubricant additives for gasoline and diesel-powered engines. Recently, however, some countries have placed limits on the amount PDDP which is considered acceptable. Therefore it is desirable to develop an alternative to PDDP and other alkylphenols for use as detergents.

There have been several efforts to prepare detergents that do not contain Cn alkyl phenols derived from oligomers of propylene. These include U.S. Pub Nos. 2008/0269351, 2011/0118160, 2011/0124539, 2011/0190185, and WO 2013/059173. Several dispersant/detergent compounds are based on the reaction of an alkenylsuccinic acid or anhydride with an amine or polyamine to produce an alkylsuccinimide or an alkenylsuccinamic acid as determined by selected conditions of reaction. Polyisobutylene succinimide dispersants are described in U.S. Pat. No. 6,770,605. Other compounds are disclosed in U.S. Pat. Nos. 3,816,353, 3,864,286, 4,058,472, 4,221,673, 4,643,838, 4,729,848, 5,510,043, 6,235,688 and 6,310,009, and U.S. Pub. Nos. US 2007/0049508, 2005/0288194, 2004/077507, 2014/130767, WO 2014193543, and EP 2374866 A1.

BRIEF DESCRIPTION

In accordance with one aspect of the exemplary embodiment, a lubricating composition includes an oil of lubricating viscosity and an N-substituted hydroxyaromatic succinimide or a salt thereof.

In accordance with another aspect of the exemplary embodiment, a method of lubricating a mechanical device includes supplying the lubricating composition to the device.

In accordance with another aspect of the exemplary embodiment, a method of forming the lubricating composition includes reacting a hydroxyaromatic amine with a succinic anhydride which includes a hydrocarbyl group of at least 8 carbon atoms, optionally bridging the reaction product and/or forming a salt thereof. A product of the reaction is combined with an oil of lubricating viscosity.

In accordance with another aspect of the exemplary embodiment, the lubricating composition is used for lubricating a mechanical device.

In accordance with another aspect of the exemplary embodiment, a hydroxyphenyl succinimide detergent includes the reaction product of an aminophenol and at least one of the group consisting of $C_8$-$C_{30}$ alkyl-substituted acid anhydrides, $C_8$-$C_{30}$ alkenyl-substituted acid anhydrides, and amino substituted acid anhydrides comprising a $C_8$-$C_{30}$ alkyl substituted amino group, or a salt thereof.

DETAILED DESCRIPTION

Aspects of the exemplary embodiment relate to a detergent useful in a lubricating composition, a lubricating composition, a method of lubrication and a use of the lubricating composition for lubricating a mechanical device.

The exemplary lubricating composition includes an oil of lubricating viscosity (or "base oil") and an N-substituted hydroxyaromatic succinimide that can serve as a detergent in the lubricating composition. The exemplary hydroxyaromatic succinimide includes a hydrocarbyl group, e.g., attached directly or indirectly to the succinimide ring, the hydrocarbyl group including least 8 carbon atoms. The hydrocarbyl group may be an alkyl or alkenyl group.

By "N-substituted," it is meant that the hydroxyaromatic group is attached to the succinimide by the nitrogen of the heterocyclic ring of the succinimide.

The exemplary N-substituted hydroxyaromatic succinimide is a succinimide derivative of a hydroxyaromatic amine. Such succinimide derivatives, in particular, N-substituted hydroxyphenyl succinimides, can have suitable detergent properties to serve as a substitute for PDDP. With performance characteristics comparable to or better than those of some existing PDDP based detergents, hydroxyphenyl succinimides can provide a metal-free alternative to PDDP.

The N-substituted hydroxyaromatic succinimide may be present in the lubricating compound in the form of a salt and/or an oligomer formed by linking two or more units of N-substituted hydroxyaromatic succinimide.

A. The Hydroxyaromatic Succinimide Compound

The N-substituted hydroxyaromatic succinimide may be represented by the general structure shown in Formula I:

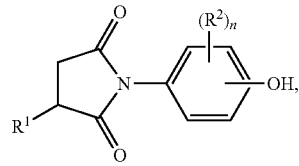

Formula I or a sulfurized and/or bridged compound, or salt thereof.
where $R^1$ is selected from the group consisting of hydrocarbyl groups of at least 8 carbon atoms, amino groups comprising a hydrocarbyl group of at least 8 carbon atoms, and alkylene amine groups comprising a hydrocarbyl group of at least 8 carbon atoms;
$R^2$ is a hydrocarbyl group;
n is 0-2.
When $R^1$ is an amino group or alkylene amine group, $R^1$ may be of the form —$(CH_2)_m NR^3 R^4$, where $R^3$ and $R^4$ may be independently selected from hydrogen and hydrocarbyl groups, and wherein at least one of $R^3$ and $R^4$ is a hydrocarbyl group of at least 8 carbon atoms.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. By predominantly hydrocarbon character, it is meant that at least 70% or at least 80% of the atoms in the substituent are hydrogen or carbon.

Examples of hydrocarbyl groups include:

(i) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

(iii) hetero substituents, that is, substituents which, while having a predominantly hydrocarbon character, may contain other than carbon in a ring or chain otherwise composed of carbon atoms.

Representative alkyl groups useful as hydrocarbyl groups include n-butyl, iso-butyl, sec-butyl, n-pentyl, amyl, neopentyl, n-hexyl, n-heptyl, secondary heptyl, n-octyl, secondary octyl, 2-ethyl hexyl, n-nonyl, secondary nonyl, undecyl, secondary undecyl, dodecyl, secondary dodecyl, tridecyl, secondary tridecyl, tetradecyl, secondary tetradecyl, hexadecyl, secondary hexadecyl, stearyl, icosyl, docosyl, tetracosyl, 2-butyloctyl, 2-butyldecyl, 2-hexyloctyl, 2-hexydecyl, 2-octyldecyl, 2-hexydodecyl, 2-octyldodecyl, 2-decyltetradecyl, 2-dodecylhexadecyl, 2-hexyldecyloctyldecyl, 2-tetradecyloctyldecy, monomethyl branched-isostearyl, and the like.

Representative alkyl groups useful as hydrocarbyl groups may include at least 1, or at least 2, or at least 3, or at least 4 carbon atoms, and in some embodiments, up to 150, or up to 100, or up to 80, or up to 40, or up to 30, or up to 28, or up to 24, or up to 20 carbon atoms. Illustrative examples include methyl, ethyl, propyl, butyl, pentyl, hexyl, heptyl, octyl, 2-ethylhexyl, nonyl, decyl, undecyl, dodecyl, tridecyl, tetradecyl, hexadecyl, stearyl, icosyl, docosyl, tetracosyl, 2-butyloctyl, 2-butyldecyl, 2-hexyloctyl, 2-hexydecyl, 2-octyldecyl, 2-hexyldodecyl, 2-octyldodecyl, 2-decyltetradecyl, 2-dodecylhexadecyl, 2-hexyldecyloctyldecyl, 2-tetradecyloctyldecyl, 4-methyl-2-pentyl, 2-propylheptyl, monomethyl branched-isostearyl, isomers thereof, mixtures thereof, and the like. Representative alicyclic groups useful as hydrocarbyl groups include cyclobutyl, cyclopentyl, and cyclohexyl groups.

Representative heteroatoms include sulfur, oxygen, nitrogen, and encompass substituents, such as pyridyl, furyl, thienyl and imidazolyl. In general, no more than two, and in one embodiment, no more than one, non-hydrocarbon substituent will be present for every ten carbon atoms in the hydrocarbyl group. In some embodiments, there are no non-hydrocarbon substituents in the hydrocarbyl group.

In Formula I, each $R^2$, where present, may be selected from hydrocarbyl groups as exemplified above. In one embodiment, each $R^2$ is an alkyl or alkenyl group of up to 20 carbon atoms or up to 12, or up to 8, or up to 6, or up to 4, or up to 2, or 1 carbon atoms. In one embodiment, n is 0.

In Formula I, $R^1$ may be a saturated or unsaturated, linear or branched, hydrocarbyl group. $R^1$ may be a hydrocarbyl group of at least 8 carbon atoms. In specific embodiments, $R^1$ may be a hydrocarbyl group of at least 10, or at least 12, or at least 14, or at least 16, or at least 18 carbon atoms. $R^1$ may be a hydrocarbyl group of up to 30 carbon atoms, or up to 28, or up to 26, or up to 24, or up to 22 carbon atoms. $R^1$ may have a molecular weight of up to 421, or up to 365.

In one embodiment, $R^1$ is selected from alkyl and alkenyl groups. Alkyl groups are saturated, linear or branched hydrocarbon radicals. Alkenyl groups are mono-unsaturated, linear or branched hydrocarbon radicals having a double bond in any position. The alkyl or alkenyl group may include a chain of at least 8 or at least 10 or at least 12 carbon atoms. Linear alkyl groups may be of the general form $(CH_2)_p CH_3$, where p may be from 7-29. Linear alkenyl groups may be of the general form $(CH_2)_q(CH=CH)(CH_2)_z CH_3$, where z=p-q-2, p may be from 7-29 and q may be at least 1. Example alkyl groups useful herein include octyl, 2-ethylhexyl, nonyl, decyl, undecyl, dodecyl, tridecyl, tetradecyl, pentadecyl, hexadecyl, heptadecyl, octadecyl, nonadecyl, icosyl, docosyl, tetracosyl, isomers thereof, mixtures thereof, and the like. Example alkenyl groups useful herein include octenyl, decenyl, undecenyl, dodecenyl, tridecenyl, tetradecenyl, pentadecenyl, hexadecenyl, heptadecenyl, octadecenyl, nonadecenyl, eicosenyl, docosenyl, tetracosenyl, hexacosenyl, heptacosenyl, isomers thereof, mixtures thereof, and the like.

In another embodiment, embodiment, $R^1$ is $—(CH_2)_n NR^3 R^4—$ where n is at least 0.

$R^3$ and $R^4$ may be independently selected from hydrogen and hydrocarbyl groups. In one embodiment, $R^3$ is a hydrocarbyl group of at least 8 carbon atoms. In another embodiment, $R^4$ is a hydrocarbyl group of at least 8 carbon atoms. In a third embodiment, both $R^3$ and $R^4$ are hydrocarbyl groups of at least 8 carbon atoms. In one embodiment m is at least 1, or at least 2. In some embodiments, m may be up to 20 or up to 10. In one embodiment, at least one of $R^3$ and $R^4$ is selected from linear alkyl and alkenyl groups of from 8-20 carbon atoms, as exemplified above for $R^1$.

In one specific embodiment, the hydroxyaromatic succinimide may be represented by the general structure shown in Formula II:

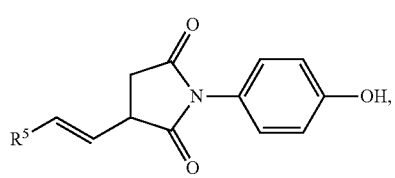

Formula II where $R^5$ may be selected from alkyl and alkenyl groups of 6 to 28 carbon atoms. Examples include pentyl, hexyl, heptyl, pentenyl, hexenyl, heptenyl, and as exemplified above for $R^5$.

In another specific embodiment, the hydroxyaromatic succinimide may be represented by the general structure shown in Formula III:

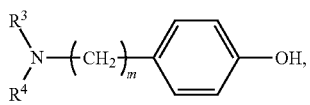

Formula III where $R^3$ and $R^4$ may be independently selected from hydrogen and hydrocarbyl groups, as described above for Formula I; and m may be at least 1.

In one embodiment, in Formula III, at least of $R^3$ and $R^4$ is an alkyl or alkenyl group.

In another embodiment, the hydroxyaromatic succinimide may be represented by the general structure shown in Formula IV:

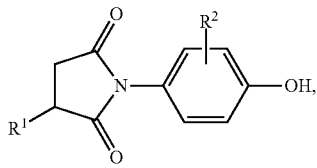

Formula IV where $R^1$ and $R^2$ may be as described above for Formula I.

Total base number (TBN), as used herein, is the quantity of acid, expressed in terms of the equivalent number of milligrams of potassium hydroxide (meq KOH), that is required to neutralize all basic constituents present in 1 gram of a sample of the lubricating oil. The TBN values reported herein are determined according to ASTM Standard D2896-11, "Standard Test Method for Base Number of Petroleum Products by Potentiometric Perchloric Acid Titration" (2011), ASTM International, West Conshohocken, Pa., 2003 DOI: 10.1520/D2896-11 (hereinafter, "D2896"). In various aspects, the neutral salt compound has a TBN of at least 20 mg of KOH/g, or at least 30 mg of KOH/g on an oil-free basis. The TBN of the neutral salt may be up to 250, or up to 200 mg KOH/g, on an oil-free basis. As an example, a $C_8$ succinic acid form of the compound may yield 174 TBN on oil free basis. In various aspects, the lubricating composition containing the compound has a TBN of at least 5, at least 6, or at least 7 mg of KOH/g, depending, in part, on the lubricating oil and other components employed.

Base Number (BN) is another method for measuring the base number, and is measured according to ASTM D4739-11, Standard Test Method for Base Number Determination by Potentiometric Hydrochloric Acid Titration, ASTM International, West Conshohocken, Pa., 2011, DOI: 10.1520/D4739-11. In various aspects, the lubricating composition has a BN of at least 2.5 mg of KOH/g, or at least 2.8 mg of KOH/g, depending, in part, on the lubricating oil and other components employed.

The hydroxyaromatic succinimide of Formula 1 may have a weight average molecular weight of at least 250, or at least 400.

In another embodiment, the compound is a bridged N-substituted hydroxyaromatic succinimide having the structure of Formula V:

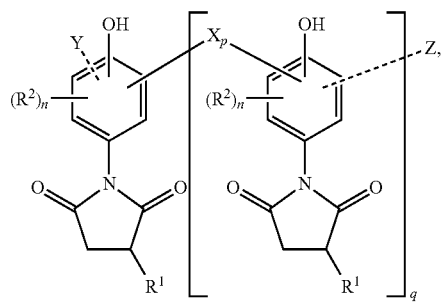

Formula V and salts thereof, where X is a sulfur or an alkylene link, where each $R^1$ and $R^2$ are independently as described above, X represents a bridging group, such as a sulfur or an alkylene bridging group (e.g., a bridge derived from one or more aldehyde monomer units, such as formaldehyde and/or propanal);

Y and Z each represent a terminal group, such as —H, —OH, a $C_1$-$C_6$ alkyl group, or a group derived from the bridging monomer (e.g., —SH, an aldehyde-derived group, such as —C(H)=O, or the like);

each n is 0-2;

q is at least 1, such as up to 5, or up to 4, or up to 3, on average, such as 1 or 2; and p is at least 1, such as up to 5, on average, or 1 or 2.

An exemplary salt may be represented by the general structure shown in Formula VI or Formula VII:

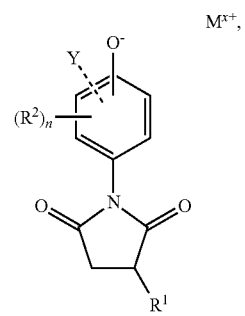

Formula VI

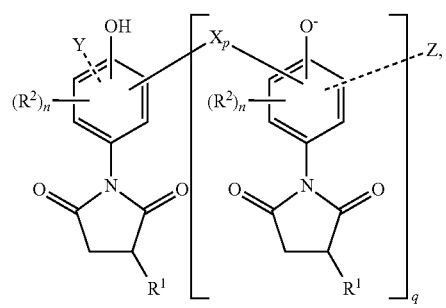

Formula VII where M represents a cation which is linked to at least one of the OH groups; and x is at least 1, such as 2 in the case of a calcium ion.

The exemplary compound of Formula VII may also be associated with a counter ion in the compound. For example, in an overbased compound, the metal ion to compound ratio may be raised above the stoichiometric amount, e.g., by bubbling $CO_2$ through the mixture to provide a carbonate counterion. As will be appreciated, these aspects can also be used in combinations thereof.

In one embodiment, the compound consists solely of elements selected from the group consisting of C, H, O, N, S and the counterion(s).

In one embodiment X is an alkylene, e.g., a methylene bridge, or a sulfur bridge. In the case of an alkylene bridge, the bridge may be up to 4 carbons in length, or up to 3 carbons in length.

As will be appreciated, these aspects can also be used in combinations thereof.

The salt of Formula VI or VII may be formed by reacting a cation or source of the cation with the compound. The compound of Formula I or V thus serves as the anion (or "substrate") in the salt. The cation or source thereof reacts with one or more of the residual OH groups to form a neutral or overbased salt of the above-described coupled polyolefin-substituted aromatic polyol.

In one embodiment, the cation is a metallic cation. The metallic cation may be derived from an alkaline earth metal, such as calcium, barium or magnesium (typically calcium), or an alkali metal, such as sodium or potassium (typically sodium). The metal cation may have an atomic weight of at least 6 or at least 12.

Exemplary metal cations include alkali metal cations, alkaline earth metal cations, transition metal cations, and combinations thereof. Examples of metal cations include $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{4+}$, $V^{3+}$, $V^{2+}$, $Nb^{4+}$, $Nb^{3+}$, $Nb^{2+}$, $Ta^{4+}$, $Ta^{3+}$, $Ta^{2+}$, $Cr^{4+}$, $Cr^{3+}$, $Cr^{2+}$, $Cr^+$, $Mo^{4+}$, $Mo^{3+}$, $Mo^{2+}$, $Mo^+$, $W^{4+}$, $W^{3+}$, $W^{2+}$, $W^+$, $Mn^{4+}$, $Mn^{3+}$, $Mn^{2+}$, $Mn^+$, $Re^{4+}$, $Re^{3+}$, $Re^{2+}$, $Re^+$, $Fe^{6+}$, $Fe^{4+}$, $Fe^{3+}$, $Fe^{2+}$, $Fe^+$, $Ru^{4+}$, $Ru^{3+}$, $Ru^{2+}$, $Os^{4+}$, $Os^{3+}$, $Os^{2+}$, $Os^+$, $Co^{5+}$, $Co^{4+}$, $Co^{3+}$, $Co^{2+}$, $Co^+$, $Rh^{4+}$, $Ru^{3+}$, $Rh^{2+}$, $Rh^+$, $Ir^{4+}$, $Ir^{3+}$, $Ir^{2+}$, $Ir^+$, $Ni^{3+}$, $Ni^{2+}$, $Ni^+$, $Pd^{4+}$, $Pd^{2+}$, $Pd^+$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{4+}$, $Au^{3+}$, $Au^{2+}$, $Au^+$, $Zn^{2+}$, $Zn^+$, $Cd^{2+}$, $Cd^+$, $Hg^{4+}$, $Hg^{2+}$, $Hg^+$, $Al^{3+}$, $Al^{2+}$, $Al^+$, $Ga^{3+}$, $Ga^+$, $In^{3+}$, $In^{2+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Sn^{4+}$, $Sn^{2+}$, $Pb^{4+}$, $Pb^{2+}$, $As^{3+}$, $As^{2+}$, $As^+$, $Sb^{3+}$, $Bi^{3+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^+$, $Ho^{3+}$, $Er^{3+}$, $Tm^{4+}$, $Tm^{3+}$, $Tm^{2+}$, $Yb^{3+}$, $Yb^{2+}$, and $Lu^{3+}$. Particularly useful are those which form stable salts, i.e., which do not decompose by more than a minor amount over the expected lifetime and operating conditions of the lubricating composition.

In one embodiment, the metallic cation is derived from a metal base such as a metal base of a hydroxide, an oxide, carbonate, or bicarbonate. The metal base may be a hydroxide or an oxide. For example the metallic cation may be derived from calcium hydroxide, calcium oxide, sodium hydroxide, sodium oxide, magnesium hydroxide, magnesium oxide, or mixture thereof.

In one embodiment, the cation is an ash-free cation. An ash-free (ashless) organic cation is an organic ion that does not contain ash-forming metals. In one embodiment, the compound in the salt form has a sulfated ash of up to 0.5 wt. %, or up to 0.4 wt. %, according to ASTM D874.

In one embodiment, the cation is a pnictogen cation. As used herein the term "pnictogens" includes the elements in column 15 of the periodic table. The non-metallic pnictogens include nitrogen and phosphorus (typically nitrogen). The pnictogen cation may be derived from a source of the cation containing a primary amine, a secondary amine, a tertiary amine, or mixture thereof. In one embodiment, the amine salt may be derived from a secondary or tertiary amine.

When the cation is pnictogen cation derived from an amine or ammonium compound, the pnictogen cation (or the amine from which it is derived) may have molecular weight of at least 260 g/mol, or at least 300 g/mol or at least 350 g/mol, or at least 500 g/mol.

The pnictogen cation may be derived from a mono-, di-, or tri-substituted amine. Specific examples include primary alkylamines, such as methylamine, ethylamine, n-propylamine, n-butylamine, n-hexylamine, n-octylamine, 2-ethylhexylamine, benzylamine, 2-phenylethylamine, cocoamine, oleylamine, and tridecylamine (CAS#86089-17-0); secondary and tertiary alkylamines such as isopropylamine, sec-butylamine, t-butylamine, cyclopentylamine, cyclohexylamine, and 1-phenylethylamine; dialkylamines, such as dimethylamine, diethylamine, dipropylamine, diisopropylamine, dibutylamine, dicyclohexylamine, di-(2-ethylhexyl)amine, dihexylamine, ethylbutylamine, N-ethylcyclohexylamine, and N-methylcyclohexylamine; cycloalkylamines, such as piperidine, N-ethylpiperidine, N,N"-dimethylpiperazine, morpholine, N-methylmorpholine, N-ethylmorpholine, N-methylpiperidine, pyrrolidine, N-methylpyrrolidine, and N-ethylpyrrolidine; and trialkylamines, such as trimethylamine, triethylamine, tripropylamine, triisopropylamine, tri-n-butylamine, trihexylamine, N, N-dimethylbenzylamine, dimethylethylamine, dimethylisopropylamine, dimethylbutylamine, and N, N-dimethylcyclohexylamine.

When the pnictogen cation includes at least one hydrocarbyl group (a quaternary ammonium ion), the pnictogen cation may be an ashless organic cation. Example ammonium cations of this type include N-substituted long chain alkenyl succinimides and aliphatic polyamines. N-substituted long chain alkenyl succinimides useful herein may be derived from an aliphatic polyamine, or mixture thereof. The aliphatic polyamine may be aliphatic polyamine such as an ethylenepolyamine, a propylenepolyamine, a butylenepolyamine, or mixture thereof. Examples of N-substituted long chain alkenyl succinimides include polyisobutylene succinimide with number average molecular weight of the polyisobutylene substituent of at least 350, or at least 500, or at least 550, or at least 750, and can be up to 5000, or up to 3000, or up to 2500. Such succinimides can be formed, for example, from high vinylidene polyisobutylene and maleic anhydride.

Example N-substituted long chain alkenyl succinimides useful herein as pnictogen cations include those derived from succinimide dispersants, which are more fully described in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, RE 26,433, 6,165,235, 7,238,650, and EP Patent Application 0 355 895 A.

Example aliphatic polyamines useful as the pnictogen cation include ethylenepolyamines, propylenepolyamines, butylenepolyamines, and mixtures thereof. Example ethylenepolyamines include ethylenediamine, diethylenetriamine, triethylenetetramine, tetraethylenepentamine, pentaethylenehexamine, polyamine still bottoms, and mixtures thereof.

In one embodiment, the exemplary compound of Formula VI or VII may be overbased, i.e., contain an excess of the metal cation in relation to the number of hydroxyl groups present in the compound. There are two common measures of basicity that are commonly used in the field of lubricant additives: Total Base Number (TBN), as measured by ASTM D2896, is a titration that measures both strong and weak bases, while ASTM D4739-11 "Standard Test Method for Base Number Determination by Potentiometric Hydrochloric Acid Titration," (BN) is a titration that measures strong bases but does not readily titrate weak bases, such as certain amines. TBN and BN are expressed as an equivalent in milligrams of potash per gram of oil (mg of KOH/g).

Total base number (TBN), as used herein, is the quantity of acid, expressed in terms of the equivalent number of milligrams of potassium hydroxide (meq KOH), that is required to neutralize all basic constituents present in 1 gram of a sample of the lubricating oil. The TBN values reported herein are determined according to ASTM Standard D2896-15, "Standard Test Method for Base Number of Petroleum Products by Potentiometric Perchloric Acid Titration" (2015), ASTM International, West Conshohocken, Pa., 2003 (hereinafter, "D2896"). In various aspects, the neutral salt compound has a TBN of at least 50 mg of KOH/g, or at least 60 mg of KOH/g on an oil-free basis. The TBN of the neutral salt may be up to 300 mg KOH/g, or up to 250 mg KOH/g, or up to 165 mg KOH/g, on an oil-free basis. In various aspects, the lubricating composition containing the compound has a TBN of at least 3 mg KOH/g, or at least 4 mg of KOH/g, or at least 6 mg of KOH/g.

The cation may serve as a basic component of the lubricating composition which, in combination with any other basic components of the lubricating composition, may provide the lubricating composition with a TBN of at least 5, or at least 8, or at least 10, or at least 15, or at least 25. The cation itself may have a TBN of at least 10 or at least or at least 15, or at least 25, or at least 50. As an example, using 0.1% of the additive on an oil free basis (having a minimum TBN of 23), this would provide a TBN contribution of at least 0.023 to the lubricating composition.

B. Method of Forming the Compound

1. Forming the Hydroxyaromatic Succinimide

The N-substituted hydroxyaromatic succinimide described above may be formed by reacting a hydroxyaromatic amine with a hydrocarbyl-substituted succinic anhydride. In one embodiment, the hydroxyaromatic amine includes an aminophenol, such as 4-aminophenol. In one embodiment, the hydroxyaromatic succinimide is an N-substituted hydroxyphenyl alkylene succinimide.

An example reaction scheme is shown in Scheme 1:

Scheme 1:

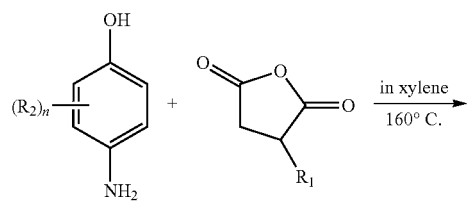

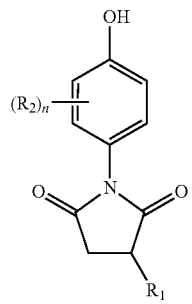

A mixture of N-substituted hydroxyphenyl succinimides is formed from a mixture of 4-aminophenol or substituted derivative thereof and an alkenyl succinic anhydride, where $R_1$ and $R_2$ can be as described above, e.g., in the presence of a solvent/diluent such as xylene at a temperature of 160° C. The solvent can then be filtered out, leaving the reaction product.

In some embodiments, the substituted succinic anhydride is selected from the group consisting of linear $C_8$-$C_{30}$ alkyl substituted acid anhydrides, linear $C_8$-$C_{30}$ alkenyl substituted acid anhydrides, and amino-substituted acid anhydrides. In some embodiments, the succinic anhydride includes at least one of hexadecenyl succinic anhydride, octadecenyl succinic anhydride, nonadecenyl succinic anhydride, eicosenyl succinic anhydride, docosenyl succinic anhydride, tetracosenyl succinic anhydride, and mixtures thereof.

Exemplary alkylene substituted succinic anhydrides useful herein include 1-dodecenyl succinic anhydride, 1-heptadecenyl succinic anhydride, 1-methyl-1-hexadecenyl succinic anhydride, 1-methyl-1-undecenyl succinic anhydride, 1-pentyl-1-heptenyl succinic anhydride, 1-heptyl-1-octenyl succinic anhydride, 1-butyl-1-decenyl succinic anhydride, 1-pentyl-3-octenyl succinic anhydride, 1-butyl-6-decenyl succinic anhydride, 2,3,5-trimethyl-4-propyl-2-heptenyl succinic anhydride, 2,4-diethyl-6-dodecenyl succinic anhydride, 3,3-dipropyl-8-decenyl succinic anhydride, 2-octenyl succinic anhydride, 6-pentacosenyl succinic anhydride, 2-ethyl-4-hexenyl succinic anhydride, 3,3-dipropyl-7-heptadecenyl succinic anhydride, octyl succinic anhydride, nonyl succinic anhydride, dodecyl succinic anhydride, eicosyl succinic anhydride, pentacosyl succinic anhydride, 2,2-dibutyldecyl succinic anhydride, 4-ethyl-3,3-dimethylheptyl succinic anhydride, 4-isobutyl-2,5-dimethyltetradecyl succinic anhydride, and mixtures thereof.

In one embodiment, the succinic anhydride is $C_{20}$-$C_{24}$ mixed alkenyl succinic anhydride. Such a mixed alkenyl succinic anhydride is available as ASA 2024 from Dixie Chemical Co., Inc.

The hydroxyaromatic succinimide may be formed in the presence or absence of solvent. The solvent may include a hydrocarbon such as toluene, xylene, diluent oil, cyclohexane or mixtures thereof. In one embodiment, the hydroxyaromatic succinimide is formed in the presence of xylene.

The reaction of the hydroxyaromatic amine with the succinic anhydride to form the hydroxyaromatic succinimide may be carried out a reaction temperature of 70° C. to 190° C., or 90° C. to 180° C., or 95° C. to 170° C.

Alkenyl succinic anhydrides may be prepared by the addition reaction of maleic anhydride and olefins, such as $C_8$-$C_{30}$ olefins. Generally, the olefin is used in molar excess, for example from about 1.5 to about 5.0 moles of olefin per mole of maleic anhydride to obtain an effective addition reaction. In other embodiments, the reaction of the olefin with the maleic anhydride is carried out in the presence of alkyl succinic anhydride, as described, for example, in U.S. Pat. No. 4,581,464.

2. Forming a Bridged N-substituted Hydroxyaromatic Succinimide

A bridged (e.g., sulfur-coupled or alkylene-coupled)N-substituted Hydroxyaromatic Succinimide of Formula V may be formed through well-known techniques.

In one embodiment, the bridged compound may be obtained/obtainable by coupling the N-substituted Hydroxyaromatic Succinimide compound of Formula I, e.g., with sulfur or formaldehyde and optionally neutralizing with a base to form a salt.

Sulfurization may be performed by contacting the N-substituted hydroxyaromatic succinimide with a sulfur source which introduces $S_x$ bridging groups between the phenol groups in the presence of a base. To form the salt the (optionally bridged) compound formed is reacted with a metal base or a pnictogen base.

An example reaction scheme is as follows:

Scheme 2:

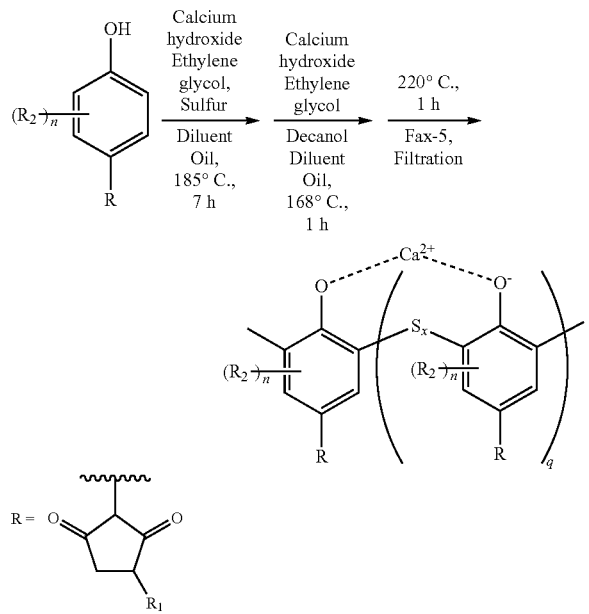

where x is from 1-5, on average, such as up to 3, or up to 2, on average.

Any suitable sulfur source can be used such as, for example, elemental sulfur or a halide thereof such as sulfur monochloride, sulfur dichloride, hydrogen sulfide, sulfur dioxide, or a sodium sulfide hydrate. The sulfur can be employed either as molten sulfur or as a solid (e.g., powder or particulate) or as a solid suspension in a compatible hydrocarbon liquid, such as ethylene glycol.

Sulfur may be employed at from 0.5 to 4 moles per mole of the compound of Formula I in the reaction system. In one embodiment, sulfur is employed at from 0.8 to 2 moles per mole of the compound.

The temperature range in which the sulfurization reaction is carried out is generally 80-250° C., e.g., 100-220° C. The reaction can be conducted under atmospheric pressure (or slightly lower) or at elevated pressures. During sulfurization a significant amount of by-product hydrogen sulfide gas is evolved. In one embodiment the reaction is carried out under vacuum to facilitate the $H_2S$ elimination.

Other sulfurization techniques which may be adapted to use herein are described, for example, in U.S. Pat. No. 2,680,096, to Walker et al., issued Jun. 1, 1954; U.S. Pat. No. 3,372,116, to Meinhardt, issued Mar. 6, 1968; U.S. Pat. No. 3,036,971, to Otto, issued May 29, 1962, U.S. Pat. No. 7,435,709, to Stonebraker, et al., issued Oct. 14, 2008, U.S. Pat. No. 8,772,209 to Mahieux, et al., issued Jul. 8, 2014, U.S. Pat. No. 9,062,271 to Jukes, et al., issued Jun. 23, 2015, and U.S. Pub. No. U.S. Pub. No. 20150045269, published Feb. 12, 2015, to Walker, et al. The 20150045269 publication, for example, describes preparation of a sulfurized alkaline earth metal (e.g., calcium) dodecylphenate by reacting dodecylphenol with calcium hydroxide or calcium oxide and an alkylene glycol. The reaction product is reacted with sulfur.

The sulfurization reaction is carried out in the presence of a base, which in one embodiment is the cation source, as described below.

In other embodiments the compound of Formula I is contacted with formaldehyde or other aldehyde, which introduces bridging groups between phenol groups in the presence of a base.

In general, sulfur coupling produces a more acidic compound which makes over-basing easier.

Formation of the salt may be performed by reaction of the optionally sulfurized compound with a basic metal compound which serves as a cation source, such as lime (calcium hydroxide/oxide) or magnesium oxide, or with a pnictogen base, in approximately equimolar amounts, with respect to the OH groups in the compound, optionally in the presence of a solvent.

Suitable basic metal compounds include hydroxides, oxides and alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide, aluminum hydroxide and the like. Representative examples of metal basic compounds with oxide functionality include lithium oxide, magnesium oxide, calcium oxide, barium oxide and the like. In one embodiment, the alkaline earth metal base is slaked lime (calcium hydroxide).

The pnictogen cation may be derived/derivable from a compound with a primary amine, a secondary amine, a tertiary amine, or mixtures thereof. Typically the amine salt may be derived from a secondary or a tertiary amine.

The amine that can be used to prepare a pnictogen may be any amine capable of salting with a protic acid. The amine may be an alkyl amine, typically a di- or tri-alkyl amine. The alkyl amine may have alkyl groups having 1 to 30, or 2 to 20, or 3 to 10 carbon atoms. Examples of a dialkyl amines include diethylamine, dipropylamine, dibutylamine, dipentylamine, dihexylamine, di-(2-ethylhexyl)amine, di-decylamine, di-dodecylamine, di-stearylamine, di-oleylamine, di-eicosylamine, or mixtures thereof. Examples of a trialkyl amine include triethylamine, tripropylamine, tributylamine, tripentylamine, trihexylamine, tri-(2-ethylhexyl) amine, tri-decylamine, tri-dodecylamine, tri-stearylamine, tri-oleylamine, tri-eicosylamine, and mixtures thereof.

The amine may also be a tertiary-aliphatic primary amine. The aliphatic group in this case may be an alkyl group containing 2 to 30, or 6 to 26, or 8 to 24 carbon atoms. Tertiary alkyl amines include monoamines such as tert-butylamine, tert-hexylamine, 1-methyl-1-amino-cyclohexane, tert-octylamine, tert-decylamine, tert-dodecylamine, tert-tetradecylamine, tert-hexadecylamine, tert-octadecylamine, tert-tetracosanylamine, and tert-octacosanylamine.

In one embodiment, the pnictogen base includes a phosphorus acid amine salt which includes an amine with $C_{11}$ to $C_{22}$ tertiary alkyl primary groups, or mixtures thereof.

In one embodiment the amine salt may be in the form of a quaternary ammonium salt. Examples of quaternary ammonium salts containing a hydroxyalkyl group, and methods for their synthesis, are disclosed in U.S. Pat. No. 3,962,104. In certain embodiments, the quaternary ammonium compound is derived from a monoamine by means of alkylation, i.e., from a tertiary amine having only a single amino group, that is, having no additional amine nitrogen atoms in any of the three hydrocarbyl groups or substituted hydrocarbyl groups attached to the tertiary amine nitrogen. In certain embodiments there are no additional amine nitrogen atoms in any of the hydrocarbyl groups or substituted hydrocarbyl groups attached to the central nitrogen in the quaternary ammonium ion. The tetraalkylammonium hydroxide may contain alkyl groups having 1 to 30, or 2 to 20, or 3 to 10 carbon atoms. The tetraalkylammonium hydroxide may include tetrapropylammonium hydroxide, tetrabutylammonium hydroxide, tetra-pentylammonium hydroxide, tetrahexylammonium hydroxide, tetra-2-ethylhexyl-ammonium hydroxide, tetradecylammonium hydroxide, or a mixture thereof.

The amine may be quaternized with a quaternizing agent, or mixture thereof.

The pnictogen base may include an aminoalkyl substituted heterocyclic compound, such as 1-(3-aminopropyl) imidazole, 4-(3-aminopropyl)morpholine, 1-(2-aminoethyl) piperidine, 3,3-diamino-N-methyldipropylamine, and 3,3-aminobis(N, N-dimethylpropylamine).

Other examples of quaternary ammonium salts and methods for preparing the same are described in U.S. Pat. Nos. 3,778,371, 4,171,959, 4,253,980, 4,326,973, 4,338,206, and 5,254,138.

When the amine salt is derived from an aromatic amine, the aromatic amine may form an ion such as a pyridinium ion, or an imidazolium ion. Certain quaternary phosphonium salts may be prepared by the reaction of phosphine with aldehydes and a halide e.g., tetrakis(hydroxymethyl)phosphonium halide (typically chloride).

A quaternary pnictogen halide compound may be a commercially available material, or it may be prepared by reaction of a tertiary amine with a hydrocarbyl halide, by known techniques. This reaction may be performed in a separate vessel or in the same vessel in which it is subsequently (or simultaneously) reacted with the oil-soluble acidic compound, which may be converted previously (or simultaneously) into its metal neutralized form.

The neutralization reaction may be carried out in a continuous or batch process by any method known to a person skilled in the art. In general, neutralization can be carried out by contacting the sulfurized or unsulfurized compound with a metal or pnictogen base under reactive conditions, e.g., in an inert-compatible liquid hydrocarbon diluent. If desired, the reaction can be conducted under an inert gas, such as nitrogen. The metal or pnictogen base may be added either in a single addition or in a plurality of additions at intermediate points during the reaction.

Neutralization may be conducted in a suitable solvent or diluent oil, such as toluene, xylene and commonly with a promoter such as an alcohol, e.g., a $C_1$ to $C_{16}$ alcohol, such as methanol, decyl alcohol, or 2-ethylhexanol; a diol, e.g., $C_2$ to $C_4$ alkylene glycols, such as ethylene glycol; and/or carboxylic acids. Suitable diluent oils include naphthenic oils and mixed oils, e.g., paraffinic. The quantity of solvent or diluent oil used may be such that the amount of solvent or oil in the final product constitutes from 15% to 65% by weight of the final product, such as from 25% to 50%.

The neutralization reaction may be conducted at temperatures above room temperature (20° C.). In general, neutralization can be carried out at a temperature of between 150-200° C. The neutralization reaction itself may take place for over 5 to 60 minutes up to 9 hours, for example, 7 hours.

In another embodiment, the salt of the bridged compound can be prepared in a one-pot method. In this method, the compound of Formula I is combined with diluent oil and ethylene glycol and heated while stirring. A metal or pnictogen base, such as hydrated lime, is added to the heated reaction mixture, e.g., in several portions. Sulfur is added to the reaction mixture, and optionally additional metal or pnictogen base is added and the mixture stirred. The reaction mixture may be vacuum stripped to remove excess solvent.

In one embodiment, an overbased compound is formed. Overbasing can be carried out either during or after one of the sulfurization and/or neutralization steps. Alternatively, sulfurization, neutralization and overbasing can be carried out simultaneously. In general, the overbasing is carried out by reaction of the salt of Formula VI or VII with an acidic overbasing compound, such as carbon dioxide or boric acid. In one embodiment, an overbasing process is by way of carbonation, i.e., a reaction with carbon dioxide. Such carbonation can be conveniently effected by addition of solvents such as aromatic solvents, alcohols or a polyols, typically an alkylene diol, e.g., ethylene glycol. Conveniently, the reaction is conducted by bubbling of gaseous carbon dioxide through the reaction mixture, optionally in the presence of sulfonic acid. Excess solvents and any water formed during the overbasing reaction can be conveniently removed by distillation either during or after the reaction.

In one embodiment, the overbasing reaction is carried out in a reactor by reacting the salt of Formula VI or VII with a source of an alkaline earth metal such as lime (i.e., an alkaline earth metal hydroxide) in the presence of carbon dioxide, and optionally in the presence of an aromatic solvent (e.g., xylene), and/or a hydrocarbyl alcohol, such as methanol. The reaction may be conducted by bubbling gaseous carbon dioxide through the reaction mixture. The carbon dioxide is introduced over a period of 1 hour to 3 hours, at a temperature ranging from 150-200° C. The degree of overbasing may be controlled by the quantity of the source of an alkaline earth metal, carbon dioxide and the reactants added to the reaction mixture and the reaction conditions used during the carbonation process.

In another embodiment, the overbasing reaction can be carried out at from 140-180° C. in the presence of a polyol, typically an alkylene diol, e.g., ethylene glycol, and/or alkanols, e.g., $C_6$ to $C_{16}$ alkanol(s), such as decyl alcohols or 2-ethyl hexanol. Excess solvent and any water formed during the overbasing reaction can be conveniently removed by distillation either during or after the reaction.

Methods for forming overbased compounds useful herein are described, for example, in U.S. Pat. Nos. 5,259,966, 6,015,778, 5,534,168, and 6,268,318, and U.S. Pub. No. 2013/0203639.

The resulting overbased salt may contain some amount of unsulfurized compound and/or its unsulfurized metal salt.

The composition containing the overbased salt of the Formula VI or VII compound may be sparged, e.g., by bubbling gas, such as air or nitrogen, at a temperature ranging from 190-250° C. through the composition. The sparging results in removing substantially all of the unsulfurized compound and salts thereof to provide a composition substantially free of the unsulfurized compound and unsulfurized salts thereof. The term "substantially free" as used herein means less than 1.5 wt. %, or less than 1 wt. %, or less than 0.3 wt. % of these unsulfurized compounds, such as 0.1-0.3 wt. %, or less.

In one embodiment, the salt thus formed does not contain any sulfonate functional groups.

In one embodiment, the salt does not contain any phosphate functional groups.

In one embodiment, the salt does not contain any borate functional groups.

The salts described above can be boronated by processes known to those skilled in the art. Boration can be accomplished either prior to, or after, the overbasing step. The boration can be accomplished by a number of boronating agents, such as boric acid, metaboric acid, orthoboric acid, alkyl borates, boron halides, polymers of boron, esters of boron and similar materials. When present, the boron content of the salt may be 0.1 wt. % to 5 wt. %, or 1 wt. % to 5 wt. %, or 2 wt. % to 4 wt. %.

Examples of suitable ethylenically unsaturated esters of boron include(meth)acrylates, fumarates and maleates which are derived from saturated alcohols, such as 2-ethylhexyl (meth)acrylate, heptyl (meth)acrylate, 2-tert-butylheptyl (meth)acrylate, octyl (meth)acrylate, 3-isopropylheptyl (meth)acrylate, nonyl (meth)acrylate, decyl (meth)acrylate, undecyl (meth)acrylate; and the corresponding fumarates and maleates. The expression "(meth)acrylates" encompasses methacrylates and acrylates and also mixtures of the two.

The salt of the compound of Formula VI or VII, in one embodiment, may comprise or consist of a) an anion composed of carbon, hydrogen, oxygen, nitrogen and optionally one or both of boron and sulfur; and b) a metallic cation, such as a calcium, magnesium or sodium cation.

3. Lubricating Composition

The optionally-bridged hydroxyaromatic succinimide compound, or salt thereof, may be present in the lubricating composition at a concentration of at least 0.1 wt. % and may be up to 20 wt. %. For example, the concentration of the compound and/or salt may be at least 0.2 wt. %, or at least 0.25 wt. %, or at least 0.3 wt. %, or at least 0.4 wt. %, or at least 0.5 wt. %, or at least 1 wt. %, of the lubricating composition. The concentration of the compound and/or salt may be up to 10 wt. %, or up to 8 wt. %, or up to 5 wt. %, or up to 2 wt. %, or up to 1.3 wt. %, of the lubricating composition. Example concentration ranges include 0.1-8 wt. %, or 0.25-5 wt. %, or 0.5-3 wt. % of the lubricating composition. The compound and/or salt may also be present in a concentrate, alone or with other additives and with a lesser amount of oil. In a concentrate, the amount of the compound and/or salt may be at least 2, or at least 3 times the concentration in the lubricating composition.

In addition to the exemplary optionally-bridged hydroxyaromatic succinimide compound or salt thereof, the exemplary lubricating composition includes an oil of lubricating viscosity and optionally one or more additional performance additives suited to providing the performance properties of a fully formulated lubricating composition, e.g., a marine diesel cylinder lubricant. Examples of these additional performance additives include viscosity modifiers, friction modifiers, antioxidants, dispersants, antiwear/antiscuffing agents, metal deactivators, extreme pressure agents, foam inhibitors, demulsifiers, pour point depressants, corrosion inhibitors, seal swelling agents, and the like, which may be used singly or in combination.

The amount of the oil of lubricating viscosity present may be typically the balance remaining after subtracting from 100 wt. %, the sum of the amount of the compound as described herein, and any other performance additives. The lubricating composition may include the oil of lubricating viscosity as a minor or major component thereof, such as at least 5 wt. %, or at least 10 wt. %, or at least 20 wt. %, or at least 30 wt. %, or at least 40 wt. %, or at least 60 wt. %, or at least 80 wt. % of the lubricating composition.

A lubricating composition may be prepared by adding the hydroxyaromatic succinimide compound to an oil of lubricating viscosity, optionally in the presence of other performance additives (as described herein below), or by adding reagents for forming the hydroxyaromatic succinimide compound to an oil of lubricating viscosity. The lubricating composition may further include additional performance additives, such as antioxidants, additional dispersants, antiwear agents, and friction modifiers. In one embodiment, the lubricating composition is metal free.

4. Oil of Lubricating Viscosity

The lubricating composition may include the oil of lubricating viscosity as a minor or major component thereof, such as at least 5 wt. %, or at least 10 wt. %, or at least 20 wt. %, or at least 30 wt. %, or at least 40 wt. %, or at least 60 wt. %, or at least 80 wt. % of the lubricating composition.

Suitable oils include natural and synthetic oils, oil derived from hydrocracking, hydrogenation, and hydrofinishing, unrefined, refined, re-refined oils or mixtures thereof. Unrefined, refined and re-refined oils, and natural and synthetic oils are described, for example, in WO2008/147704 and US Pub. No. 2010/197536. Synthetic oils may also be produced by Fischer-Tropsch reactions and typically may be hydroisomerized Fischer-Tropsch hydrocarbons or waxes. Oils may be prepared by a Fischer-Tropsch gas-to-liquid synthetic procedure as well as other gas-to-liquid procedures.

Oils of lubricating viscosity may also be defined as specified in April 2008 version of "Appendix E—API Base Oil Interchangeability Guidelines for Passenger Car Motor Oils and Diesel Engine Oils", section 1.3 Sub-heading 1.3. "Base Stock Categories". The API Guidelines are also summarized in U.S. Pat. No. 7,285,516. The five base oil groups are as follows: Group I (sulfur content >0.03 wt. %, and/or <90 wt. % saturates, viscosity index 80-120); Group II (sulfur content <0.03 wt. %, and >90 wt. % saturates, viscosity index 80-120); Group III (sulfur content <0.03 wt. %, and >90 wt. % saturates, viscosity index >120); Group IV (all polyalphaolefins (PAOs)); and Group V (all others not included in Groups I, II, III, or IV). The exemplary oil of lubricating viscosity includes an API Group I, Group II, Group III, Group IV, Group V oil, or mixtures thereof. In some embodiments, the oil of lubricating viscosity is an API Group I, Group II, Group III, or Group IV oil, or mixtures thereof. In some embodiments, the oil of lubricating viscosity is an API Group I, Group II, or Group III oil, or mixture thereof. In one embodiment the oil of lubricating viscosity may be an API Group II, Group III mineral oil, a Group IV synthetic oil, or mixture thereof. In some embodiments, at least 5 wt. %, or at least 10 wt. %, or at least 20 wt. %, or at least 40 wt. % of the lubricating composition is a polyalphaolefin (Group IV).

The lubricating composition disclosed herein may have a SAE viscosity grade of XW-Y, wherein X may be 0, 5, 10 or 15; and Y may be 16, 20, 30 or 40.

The oil of lubricating viscosity may have a kinematic viscosity of up to 30 mm$^2$/s or up to 25 mm$^2$/s (cSt) at 100° C. and can be at least 12 mm$^2$/s at 100° C., and in other embodiments at least 15 mm$^2$/s. As used herein, kinematic viscosity is determined at 100° C. by ASTM D445-14, "Standard Test Method for Kinematic Viscosity of Transparent and Opaque Liquids (and Calculation of Dynamic Viscosity)," ASTM International, West Conshohocken, Pa., 2003, DOI: 10.1520/D0445-14 and may be referred to as KV_100.

The viscosity grade of cylinder oils suited to use in 2-stroke marine diesel engines may be from SAE-40 to SAE-60, which corresponds to a KV_100 of 12.5 to 26 mm$^2$/s. SAE-50 grade oils, for example, have a KV_100 of 16.3-21.9 mm$^2$/s. Cylinder oils for 2-stroke marine diesel engines may be formulated to achieve a KV_100 of 19 to 21.5 mm$^2$/s. This viscosity can be obtained by a mixture of additives and base oils, for example containing mineral bases of Group I such as Neutral Solvent (for example 500 NS or 600 NS) and Bright Stock bases. Any other combination of mineral or synthetic bases or bases of vegetable origin having, in mixture with the additives, a viscosity compatible with the grade SAE 50 can be used.

As an example, an oil formulation suited to use as a cylinder lubricant for low-speed 2-stroke marine diesel engines contains 18 to 25 wt. % of a Group I base oil of a BSS type (distillation residue, with a KV_100 of 28-32 mm$^2$/s, with a density at 15° C. of 895-915 kg/m$^3$), and 50 to 60 wt. % of a Group I base oil of a SN 600 type (distillate, with a density at 15° C. of 880-900 kg/m$^3$, with a KV_100 of about 12 mm$^2$/s).

In certain embodiments, the lubricating composition may contain synthetic ester base fluids. Synthetic esters may have a kinematic viscosity measured at 100° C. of 2.5 mm$^2$/s to 30 mm$^2$/s. In one embodiment, the lubricating composition comprises less than 50 wt. % of a synthetic ester base fluid with a KV_100 of at least 5.5 mm$^2$/s, or at least 6 mm$^2$/s, or at least 8 mm$^2$/s.

Exemplary synthetic oils include poly-alpha olefins, polyesters, poly-acrylates, and poly-methacrylates, and co-polymers thereof. Example synthetic esters include esters of a dicarboxylic acid (e.g., selected from phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, and alkenyl malonic acids) with an alcohol (e.g., selected from butyl alcohol, hexyl alcohol, dodecyl alcohol, 2-ethylhexyl alcohol, ethylene glycol, diethylene glycol monoether, and propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and from polyol ethers such as neopentyl glycol, trimethylolpropane, pentaerythritol, dipentaerythritol, and tripentaerythritol. Esters can also be monoesters, such as are available under the trade name Priolube 1976™ ($C_{18}$-alkyl-COO—$C_{20}$ alkyl).

Synthetic ester base oils may be present in the lubricating composition of the invention in an amount less than 50 wt. % of the composition, or less than 40 weight %, or less than 35 weight %, or less than 28 weight %, or less than 21 weight %, or less than 17 weight %, or less than 10 weight %, or less than 5 weight % of the composition. In one embodiment, the lubricating composition of the invention is free of, or substantially free of, a synthetic ester base fluid having a KV_100 of at least 5.5 mm$^2$/s.

Example natural oils include animal and vegetable oils, such as long chain fatty acid esters. Examples include linseed oil, sunflower oil, sesame seed oil, beef tallow oil, lard oil, palm oil, castor oil, cottonseed oil, corn oil, peanut oil, soybean oil, olive oil, whale oil, menhaden oil, sardine oil, coconut oil, palm kernel oil, babassu oil, rape oil, and soya oil.

The amount of the oil of lubricating viscosity present is typically the balance remaining after subtracting from 100 weight % the sum of the amount of the exemplary aminocarboxylate compound and the other performance additives.

Other Performance Additives

In addition to the exemplary hydroxyaromatic succinimide compound(s) disclosed herein, the lubricating composition may further include one or more of the following additional performance additives: antioxidants, dispersants, viscosity modifiers, antiwear/antiscuffing agents, metal deactivators, friction modifiers, extreme pressure agents, foam inhibitors, demulsifiers, pour point depressants, corrosion inhibitors, seal swelling agents, and the like.

A. Detergents

The lubricating composition optionally further includes at least one detergent. Exemplary detergents useful herein include overbased metal-containing detergents. The metal of the metal-containing detergent may be zinc, sodium, calcium, barium, or magnesium. The overbased metal-containing detergent may be chosen from sulfonates, non-sulfur containing phenates, sulfur containing phenates, salixarates, salicylates, and mixtures thereof, or borated equivalents thereof. The overbased detergent may be borated with a borating agent such as boric acid.

The overbased metal-containing detergent may also include "hybrid" detergents formed with mixed surfactant systems including phenate and/or sulfonate components, e.g., phenate/salicylates, sulfonate/phenates, sulfonate/salicylates, sulfonates/phenates/salicylates, as described, for example, in U.S. Pat. Nos. 6,429,178; 6,429,179; 6,153,565; and 6,281,179. Where a hybrid sulfonate/phenate detergent is employed, the hybrid detergent can be considered equivalent to amounts of distinct phenate and sulfonate detergents introducing like amounts of phenate and sulfonate soaps, respectively.

Example overbased metal-containing detergents include zinc, sodium, calcium and magnesium salts of sulfonates, phenates (including sulfur-containing and non-sulfur containing phenates), salixarates and salicylates. Such overbased sulfonates, salixarates, phenates and salicylates may have a total base number of 120 to 700, or 250 to 600, or 300 to 500 (on an oil free basis).

Typically, an overbased metal-containing detergent may be a zinc, sodium, calcium or magnesium salt of a sulfonate, a phenate, sulfur containing phenate, salixarate or salicylate. Overbased sulfonates, salixarates, phenates and salicylates typically have a total base number of 120 to 700 TBN. Overbased sulfonates typically have a total base number of 120 to 700, or 250 to 600, or 300 to 500 (on an oil free basis).

The overbased sulfonate detergent may have a metal ratio of 12 to less than 20, or 12 to 18, or 20 to 30, or 22 to 25.

In one embodiment, the lubricating composition is substantially free of overbased metal-containing detergents. By substantially free, it is meant that the concentration of all overbased metal-containing detergents in the lubricating composition is less than 0.1 wt. %, or less than 0.05 wt. %, or less than 0.01 wt. %, or less than 0.001 wt. %.

Example sulfonate detergents include linear and branched alkylbenzene sulfonate detergents, and mixtures thereof, which may have a metal ratio of at least 8, as described, for example, in U.S. Pub. No. 2005065045. Linear alkyl benzenes may have the benzene ring attached anywhere on the linear chain, usually at the 2, 3, or 4 position, or be mixtures thereof. Linear alkylbenzene sulfonate detergents may be particularly useful for assisting in improving fuel economy.

In one embodiment, the alkylbenzene sulfonate detergent may be a branched alkylbenzene sulfonate, a linear alkylbenzene sulfonate, or mixtures thereof.

In one embodiment, the lubricating composition may be free of linear alkylbenzene sulfonate detergent. The sulfonate detergent may be a metal salt of one or more oil-soluble alkyl toluene sulfonate compounds as disclosed in U.S. Pub. No. 20080119378.

The lubricating composition may include at least 0.01 wt. % or at least 0.1 wt. %, detergent, and in some embodiments, up to 2 wt. %, or up to 1 wt. % detergent.

B. Antioxidants

The lubricating composition optionally further includes at least one antioxidant. Exemplary antioxidants useful herein include phenolic and aminic antioxidants, such as diarylamines, alkylated diarylamines, hindered phenols, and mixtures thereof. The diarylamine or alkylated diarylamine may be a phenyl-a-naphthylamine (PANA), an alkylated diphenylamine, an alkylated phenylnapthylamine, or mixture thereof. Example alkylated diphenylamines include dinonyl diphenylamine, nonyl diphenylamine, octyl diphenylamine, dioctyl diphenylamine, didecyl diphenylamine, decyl diphenylamine, and mixtures thereof. Example alkylated diarylamines include octyl, dioctyl, nonyl, dinonyl, decyl and didecyl phenylnapthylamines. Hindered phenol antioxidants often contain a secondary butyl and/or a tertiary butyl group as a steric hindering group. The phenol group may be further substituted with a hydrocarbyl group (e.g., a linear or branched alkyl) and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol, 4-butyl-2,6-di-tert-butylphenol, and 4-dodecyl-2,6-di-tert-butylphenol. In one embodiment, the hindered phenol antioxidant may be an ester, such as those described in U.S. Pat. No. 6,559,105. One such hindered phenol ester is sold as Irganox™ L-135, obtainable from Ciba.

When present, the lubricating composition may include at least 0.1 wt. % or at least 0.5 wt. %, or at least 1 wt. % antioxidant, and in some embodiments, up to 3 wt. %, or up to 2.75 wt. %, or up to 2.5 wt. % antioxidant.

C. Dispersants

The lubricating composition optionally further includes at least one dispersant other than the exemplary compound. Exemplary dispersants include succinimide dispersants, Mannich dispersants, succinimide dispersants, and polyolefin succinic acid esters, amides, and ester-amides, and mixtures thereof. The succinimide dispersant, where present, may be as described above for the succinimides described as useful for cation M.

The succinimide dispersant may be derived from an aliphatic polyamine, or mixtures thereof. The aliphatic polyamine may be an ethylenepolyamine, a propylenepolyamine, a butylenepolyamine, or a mixture thereof. In one embodiment the aliphatic polyamine may be an ethylenepolyamine. In one embodiment the aliphatic polyamine may be chosen fromethylenediamine, diethylenetriamine, triethylenetetramine, tetraethylenepentamine, pentaethylenehexamine, polyamine still bottoms, and mixtures thereof.

In one embodiment, the dispersant may be a polyolefin succinic acid ester, amide, or ester-amide. A polyolefin succinic acid ester-amide may be a polyisobutylene succinic acid reacted with an alcohol (such as pentaerythritol) and a polyamine as described above. Example polyolefin succinic acid esters include polyisobutylene succinic acid esters of pentaerythritol and mixture thereof.

The dispersant may be an N-substituted long chain alkenyl succinimide. An example of an N-substituted long chain alkenyl succinimide is polyisobutylene succinimide. Typically the polyisobutylene from which polyisobutylene succinic anhydride is derived has a number average molecular weight of 350 to 5000, or 550 to 3000 or 750 to 2500. Succinimide dispersants and their preparation are disclosed, for example, in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and 6,165,235, and 7,238,650 and EP Patent Application 0 355 895 A.

The succinimide dispersant may comprise a polyisobutylene succinimide, wherein the polyisobutylene from which polyisobutylene succinimide is derived has a number average molecular weight of 350 to 5000, or 750 to 2500.

The exemplary dispersants may also be post-treated by conventional methods by a reaction with any of a variety of agents. Among these are boron compounds (such as boric acid), urea, thiourea, dimercaptothiadiazoles, carbon disulfide, aldehydes, ketones, carboxylic acids, such as terephthalic acid, hydrocarbon-substituted succinic anhydrides, maleic anhydride, nitriles, epoxides, and phosphorus compounds. In one embodiment the post-treated dispersant is borated. In one embodiment the post-treated dispersant is reacted with dimercaptothiadiazoles. In one embodiment the post-treated dispersant is reacted with phosphoric or phosphorous acid. In one embodiment the post-treated dispersant is reacted with terephthalic acid and boric acid (as described in U.S. Pub. No. 2009/0054278.

When present, the lubricating composition may include at least 0.01 wt. %, or at least 0.1 wt. %, or at least 0.5 wt. %, or at least 1 wt. % dispersant, and in some embodiments, up to 20 wt. %, or up to 15 wt. %, or up to 10 wt. %, or up to 6 wt. % or up to 3 wt. % dispersant.

D. Anti-wear Agents

The lubricating composition optionally further includes at least one antiwear agent. Examples of suitable antiwear agents suitable for use herein include titanium compounds, tartrates, tartrimides, oil soluble amine salts of phosphorus compounds, sulfurized olefins, metal dihydrocarbyldithiophosphates (such as zinc dialkyldithiophosphates), phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulfides. The antiwear agent may in one embodiment include a tartrate, or tartrimide as described in U.S. Pub. Nos. 2006/0079413; 2006/0183647; and 2010/0081592. The tartrate or tartrimide may contain alkyl-ester groups, where the sum of carbon atoms on the alkyl groups is at least 8. The antiwear agent may, in one embodiment, include a citrate as is disclosed in US Pub. No. 20050198894.

The lubricating composition may in one embodiment further include a phosphorus-containing antiwear agent. Example phosphorus-containing antiwear agents include zinc dialkyldithiophosphates, phosphites, phosphates, phosphonates, and ammonium phosphate salts, and mixtures thereof.

When present, the lubricating composition may include at least 0.01 wt. %, or at least 0.1 wt. %, or at least 0.5 wt. % antiwear agent, and in some embodiments, up to 3 wt. %, or up to 1.5 wt. %, or up to 0.9 wt. antiwear agent.

E. Oil Soluble Titanium Compounds

The lubricating composition may include one or more oil-soluble titanium compounds, which may function as antiwear agents, friction modifiers, antioxidants, deposit control additives, or more than one of these functions. Example oil-soluble titanium compounds are disclosed in U.S. Pat. No. 7,727,943 and U.S. Pub. No. 2006/0014651. Example oil soluble titanium compounds include titanium (IV) alkoxides, such as titanium (IV) isopropoxide and titanium (IV) 2-ethylhexoxide. Such alkoxides may be formed from a monohydric alcohol, a vicinal 1,2-diol, a polyol, or mixture thereof. The monohydric alkoxides may have 2 to 16, or 3 to 10 carbon atoms. In one embodiment, the titanium compound comprises the alkoxide of a vicinal 1,2-diol or polyol. 1,2-vicinal diols include fatty acid monoesters of glycerol, where the fatty acid may be, for example, oleic acid. Other example oil soluble titanium compounds include titanium carboxylates, such as titanium neodecanoate.

When present in the lubricating composition, the amount of oil-soluble titanium compounds is included as part of the antiwear agent.

F. Extreme Pressure (EP) Agents

The lubricating composition may include an extreme pressure agent.

Example extreme pressure agents that are soluble in the oil include sulfur- and chlorosulfur-containing EP agents, dimercaptothiadiazole or $CS_2$ derivatives of dispersants (typically succinimide dispersants), derivative of chlorinated hydrocarbon EP agents and phosphorus EP agents. Examples of such EP agents include chlorinated wax; sulfurized olefins (such as sulfurized isobutylene), hydrocarbyl-substituted 2,5-dimercapto-1,3,4-thiadiazoles and oligomers thereof, organic sulfides and polysulfides, such as dibenzyl disulfide, bis-(chlorobenzyl) disulfide, dibutyl tetrasulfide, sulfurized methyl ester of oleic acid, sulfurized alkylphenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters, such as dihydrocarbon and trihydrocarbon phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenol phosphite; metal thiocarbamates, such as zinc dioctyldithiocarbamate and barium heptylphenol diacid; amine salts of alkyl and dialkylphosphoric acids or derivatives including, for example, the amine salt of a reaction product of a dialkyldithiophosphoric acid with propylene oxide and subsequently followed by a further reaction with $P_2O_5$; and mixtures thereof. Some useful extreme pressure agents are described in U.S. Pat. No. 3,197,405.

When present, the lubricating composition may include at least 0.01 wt. %, or at least 0.1 wt. %, or at least 0.5 wt. % extreme pressure agent, and in some embodiments, up to 3 wt. %, or up to 1.5 wt. %, or up to 0.9 wt. % of the extreme pressure agent.

G. Foam Inhibitors

The lubricating composition may include a foam inhibitor. Foam inhibitors that may be useful in the lubricant composition include polysiloxanes; copolymers of ethyl acrylate and 2-ethylhexylacrylate and optionally vinyl acetate; demulsifiers including fluorinated polysiloxanes, trialkyl phosphates, polyethylene glycols, polyethylene oxides, polypropylene oxides and (ethylene oxide-propylene oxide) polymers.

H. Viscosity Modifiers

The lubricating composition may include a viscosity modifier. Viscosity modifiers (also sometimes referred to as viscosity index improvers or viscosity improvers) useful in the lubricant composition are usually polymers, including polyisobutenes, polymethacrylates (PMA) and polymethacrylic acid esters, diene polymers, polyalkylstyrenes, esterified styrene-maleic anhydride copolymers, hydrogenated alkenylarene-conjugated diene copolymers and polyolefins also referred to as olefin copolymer or OCP. PMAs are prepared from mixtures of methacrylate monomers having different alkyl groups. The alkyl groups may be either straight chain or branched chain groups containing from 1 to 18 carbon atoms. Most PMAs are viscosity modifiers as well as pour point depressants. In one embodiment, the viscosity modifier is a polyolefin comprising ethylene and one or more higher olefin, such as propylene.

When present, the lubricating composition may include at least 0.01 wt. %, or at least 0.1 wt. %, or at least 0.3 wt. %, or at least 0.5 wt. % polymeric viscosity modifiers, and in some embodiments, up to 10 wt. %, or up to 5 wt. %, or up to 2.5 wt. % polymeric viscosity modifiers.

I. Corrosion Inhibitors and Metal Deactivators

The lubricating composition may include a corrosion inhibitor. Corrosion inhibitors/metal deactivators that may be useful in the exemplary lubricating composition include fatty amines, octylamine octanoate, condensation products of dodecenyl succinic acid or anhydride, and a fatty acid such as oleic acid with a polyamine, derivatives of benzotriazoles (e.g., tolyltriazole), 1,2,4-triazoles, benzimidazoles, 2-alkyldithiobenzimidazoles and 2-alkyldithiobenzothiazoles.

J. Pour Point Depressants

The lubricating composition may include a pour point depressant. Pour point depressants that may be useful in the exemplary lubricating composition include polyalphaolefins, esters of maleic anhydride-styrene copolymers, polymethacrylates, polyacrylates, and polyacrylamides.

K. Friction Modifiers

The lubricating composition may include a friction modifier. Friction modifiers that may be useful in the exemplary lubricating composition include fatty acid derivatives such as amines, esters, epoxides, fatty imidazolines, condensation products of carboxylic acids and polyalkylene-polyamines and amine salts of alkylphosphoric acids. The friction modifier may be an ash-free friction modifier. Such friction modifiers are those which typically not produce any sulfated ash when subjected to the conditions of ASTM D 874. An additive is referred to as "non-metal containing" if it does not contribute metal content to the lubricant composition. As used herein the term "fatty alkyl" or "fatty" in relation to friction modifiers means a carbon chain having 8 to 30 carbon atoms, typically a straight carbon chain.

In one embodiment, the ash-free friction modifier may be represented by the formula:

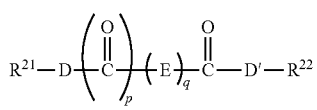

where D and D' are independently selected from —O—, >NH, >NR$^{23}$, an imide group formed by taking together both D and D groups and forming a R$^{21}$—N<group between two >C=O groups; E is selected from —R$^{24}$—O—R$^{25}$—, >CH$_2$, >CHR$^{26}$, >CR$^{26}$R$^{27}$, >C(OH)(CO$_2$R$^{22}$), >C(CO$_2$R$^{22}$)$_2$, and >CHOR$^{28}$; where R$^{24}$ and R$^{25}$ are independently selected from >CH$_2$, >CHR$^{26}$, >CR$^{26}$R$^{27}$, >C(OH)(CO$_2$R$^{22}$), and >CHOR$^{28}$; q is 0 to 10, with the proviso that when q=1, E is not >CH$_2$, and when n=2, both Es are not >CH$_2$; p is 0 or 1; R$^{21}$ is independently hydrogen or a hydrocarbyl group, typically containing 1 to 150 carbon atoms, with the proviso that when R$^{21}$ is hydrogen, p is 0, and q is more than or equal to 1; R$^{22}$ is a hydrocarbyl group, typically containing 1 to 150 carbon atoms; R$^{23}$, R$^{24}$, R$^{25}$, R$^{26}$ and R$^{27}$ are independently hydrocarbyl groups; and R$^{28}$ is hydrogen or a hydrocarbyl group, containing 1 to 150 carbon atoms, or 4 to 32 carbon atoms, or 8 to 24 carbon atoms. In certain embodiments, the hydrocarbyl groups R$^{23}$, R$^{24}$, and R$^{25}$, may be linear or predominantly linear alkyl groups.

In certain embodiments, the ash-free friction modifier is a fatty ester, amide, or imide of various hydroxy-carboxylic acids, such as tartaric acid, malic acid lactic acid, glycolic acid, and mandelic acid. Examples of suitable materials include tartaric acid di(2-ethylhexyl) ester (i.e., di(2-ethylhexyl)tartrate), di(C$_8$-C$_{10}$) tartrate, di(C$_{12-15}$) tartrate, di-oleyl tartrate, oleyl tartrimide, and oleyl maleimide.

In certain embodiments, the ash-free friction modifier may be chosen from long chain fatty acid derivatives of amines, fatty esters, or fatty epoxides;

fatty imidazolines such as condensation products of carboxylic acids and polyalkylene-polyamines; amine salts of alkylphosphoric acids; fatty alkyl tartrates; fatty alkyl tartrimides; fatty alkyl tartramides; fatty phosphonates; fatty phosphites; borated phospholipids, borated fatty epoxides; glycerol esters; borated glycerol esters; fatty amines; alkoxylated fatty amines; borated alkoxylated fatty amines; hydroxyl and polyhydroxy fatty amines including tertiary hydroxy fatty amines; hydroxy alkyl amides; metal salts of fatty acids; metal salts of alkyl salicylates; fatty oxazolines; fatty ethoxylated alcohols; condensation products of carboxylic acids and polyalkylene polyamines; or reaction products from fatty carboxylic acids with guanidine, aminoguanidine, urea, or thiourea and salts thereof.

Friction modifiers may also encompass materials such as sulfurized fatty compounds and olefins, sunflower oil or soybean oil monoester of a polyol and an aliphatic carboxylic acid.

In another embodiment the friction modifier may be a long chain fatty acid ester. In another embodiment the long chain fatty acid ester may be a mono-ester and in another embodiment the long chain fatty acid ester may be a triglyceride.

The amount of the ash-free friction modifier in a lubricant may be 0.1 to 3 wt. % (or 0.12 to 1.2 or 0.15 to 0.8 wt. %). The material may also be present in a concentrate, alone or with other additives and with a lesser amount of oil. In a concentrate, the amount of material may be two to ten times the above concentration amounts.

Molybdenum compounds are also known as friction modifiers. The exemplary molybdenum compound does not contain dithiocarbamate moieties or ligands.

Nitrogen-containing molybdenum materials include molybdenum-amine compounds, as described in U.S. Pat. No. 6,329,327, and organomolybdenum compounds made from the reaction of a molybdenum source, fatty oil, and a diamine as described in U.S. Pat. No. 6,914,037. Other molybdenum compounds are disclosed in U.S. Pub. No. 20080280795. Molybdenum amine compounds may be obtained by reacting a compound containing a hexavalent molybdenum atom with a primary, secondary or tertiary amine represented by the formula NR$^{29}$R$^{39}$R$^{31}$, where each of R$^{29}$, R$^{39}$ and R$^{31}$ is independently hydrogen or a hydrocarbyl group of 1 to 32 carbon atoms and wherein at least one of R$^{29}$, R$^{39}$ and R$^{31}$ is a hydrocarbyl group of 4 or more carbon atoms or represented by the formula:

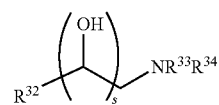

where R$^{32}$ represents a chain hydrocarbyl group having 10 or more carbon atoms, s is 0 or 1, R$^{33}$ and/or R$^{34}$ represents a hydrogen atom, a hydrocarbyl group, an alkanol group or an alkyl amino group having 2 to 4 carbon atoms, and when s=0, both R$^{33}$ and R$^{34}$ are not hydrogen atoms or hydrocarbon groups.

Specific examples of suitable amines include monoalkyl (or alkenyl) amines such as tetradecylamine, stearylamine, oleylamine, beef tallow alkylamine, hardened beef tallow alkylamine, and soybean oil alkylamine; dialkyl(or alkenyl) amines such as N-tetradecylmethylamine, N-pentadecylmethylamine, N-hexadecylmethylamine, N-stearylmethylamine, N-oleylmethylamine, N-cococylmethylamine, N-beef tallow alkyl methylamine, N-hardened beef tallow alkyl methylamine, N-soybean oil alkyl methylamine, ditetradecylamine, dipentadecylamine, dihexadecylamine, distearylamine, dioleylamine, bis(2-hexyldecyl)amine, bis(2-octyldodecyl)amine, bis(2-decyltetradecyl)amine, beef tallow dialkylamine, hardened beef tallow dialkylamine, and soybean oil dialkylamine; and trialk(en)ylamines such as tetradecyldimethylamine, hexadecyldimethylamine, octadecyldimethylamine, beef tallow alkyldimethylamine, hardened beef tallow alkyldimethylamine, soybean oil alkyldimethylamine, dioleylmethylamine, tritetradecylamine, tristearylamine, and trioleylamine. Suitable secondary amines have two alkyl (or alkenyl) groups with 14 to 18 carbon atoms.

Examples of the compound containing the hexavalent molybdenum atom include molybdenum trioxides or hydrates thereof (MoO$_3$.nH$_2$O), molybdenum acid (H$_2$MoO$_4$), alkali metal molybdates (Q$_2$MoO$_4$) wherein Q represents an alkali metal, such as sodium or potassium, ammonium molybdates {(NH$_4$)$_2$MoO$_4$ or heptamolybdate (NH$_4$)$_6$[Mo$_7$O$_{24}$].4H$_2$O}, MoOCl$_4$, MoO$_2$Cl$_2$, MoO$_2$Br$_2$, Mo$_2$O$_3$Cl$_6$, and the like. Molybdenum trioxides or hydrates thereof, molybdenum acid, alkali metal molybdates and ammonium molybdates are often suitable because of their availability. In one embodiment, the lubricating composition comprises molybdenum amine compound.

Other organomolybdenum compounds of the invention may be the reaction products of fatty oils, mono-alkylated alkylene diamines and a molybdenum source. Materials of this sort are generally made in two steps, a first step involving the preparation of an aminoamide/glyceride mixture at high temperature, and a second step involving incorporation of the molybdenum.

Examples of fatty oils that may be used include cottonseed oil, groundnut oil, coconut oil, linseed oil, palm kernel oil, olive oil, corn oil, palm oil, castor oil, rapeseed oil (low or high erucic acids), soyabean oil, sunflower oil, herring oil, sardine oil, and tallow. These fatty oils are generally known as glyceryl esters of fatty acids, triacylglycerols or triglycerides.

Examples of some mono-alkylated alkylene diamines that may be used include methylaminopropylamine, methylaminoethylamine, butylaminopropylamine, butylaminoethylamine, octylaminopropylamine, octylaminoethylamine, dodecylaminopropylamine, dodecylaminoethylamine, hexadecylaminopropylamine, hexadecylaminoethylamine, octadecyl-aminopropylamine, octadecylaminoethylamine, isopropyloxypropyl-1,3-diaminopropane, and octyloxypropyl-1,3-diaminopropane. Mono-alkylated alkylene diamines derived from fatty acids may also be used. Examples include N-coco alkyl-1,3-propanediamine (Duomeen®C), N-tall oil alkyl-1,3-propanediamine (Duomeen®T) and N-oleyl-1,3-propanediamine (Duomeen®O), all commercially available from Akzo Nobel.

Sources of molybdenum for incorporation into the fatty oil/diamine complex are generally oxygen-containing molybdenum compounds include, similar to those above, ammonium molybdates, sodium molybdate, molybdenum oxides and mixtures thereof. One suitable molybdenum source comprises molybdenum trioxide ($MoO_3$).

Nitrogen-containing molybdenum compounds which are commercially available include, for example, Sakuralube® 710 available from Adeka which is a molybdenum amine compound, and Molyvan® 855, available from R.T. Vanderbilt.

The nitrogen-containing molybdenum compound may be present in the lubricant composition at 0.005 to 2 wt. % of the composition, or 0.01 to 1.3 wt. %, or 0.02 to 1.0 wt. % of the composition. The molybdenum compound may provide the lubricant composition with 0 to 1000 ppm, or 5 to 1000 ppm, or 10 to 750 ppm 5 ppm to 300 ppm, or 20 ppm to 250 ppm of molybdenum.

L. Demulsifiers

Demulsifiers useful herein include trialkyl phosphates, and various polymers and copolymers of ethylene glycol, ethylene oxide, propylene oxide, and mixtures thereof.

M. Seal Swell Agents

Seal swell agents useful herein include sulfolene derivatives such as Exxon Necton-37™ (FN 1380) and Exxon Mineral Seal Oil™ (FN 3200).

5. Example Lubricating Compositions

An engine lubricant in different embodiments may have a composition as illustrated in Table 1. All additives are expressed on an oil-free basis.

TABLE 1

Example Lubricating Composition

| Additive | Embodiments (wt. %) | | |
|---|---|---|---|
| | A | B | C |
| Example compound | 0.1 to 5 | 0.2 to 3 | 0.5 to 2 |
| Overbased Detergent | 2 to 9 | 3 to 8 | 3 to 5 |
| Dispersant Viscosity Modifier | 0 to 5 | 0 to 4 | 0.05 to 2 |
| Dispersant | 0 to 12 | 0 to 8 | 0.5 to 6 |

TABLE 1-continued

Example Lubricating Composition

| Additive | Embodiments (wt. %) | | |
|---|---|---|---|
| | A | B | C |
| Antioxidant | 0.1 to 13 | 0.1 to 10 | 0.5 to 5 |
| Antiwear Agent | 0.1 to 15 | 0.1 to 10 | 0.3 to 5 |
| Friction Modifier | 0.01 to 6 | 0.05 to 4 | 0.1 to 2 |
| Viscosity Modifier | 0 to 10 | 0.5 to 8 | 1 to 6 |
| Any Other Performance Additive | 0 to 10 | 0 to 8 | 0 to 6 |
| Oil of Lubricating Viscosity | Balance to 100% | Balance to 100% | Balance to 100% |

Use of the Lubricating Composition

The end use of the lubricating composition described herein includes use as a cylinder lubricant for an internal combustion engine, such as a 2-stroke marine diesel engine, but may also find use as an engine oil for passenger car, heavy, medium and light duty diesel vehicles, small engines such as motorcycle and 2-stroke oil engines, as a driveline lubricant, including gear and automatic transmission oils, and for other industrial oils, such as hydraulic lubricants.

An exemplary method of lubricating a mechanical device, such as a 2-stroke marine diesel engine cylinder, includes supplying the exemplary lubricating composition to the device.

Generally, the lubricating composition is added to the lubricating system of an internal combustion engine, which then delivers the lubricating composition to the cylinder of the engine, during its operation, where it may be combusted with the fuel.

The internal combustion engine may be a diesel-fuelled engine, such as a 2-stroke marine diesel engine, or a gasoline fuelled engine, a natural gas fuelled engine, a mixed gasoline/alcohol fuelled engine, or a biodiesel fuelled engine. The internal combustion engine may be a 2-stroke or 4-stroke engine.

In one embodiment the disclosed technology provides a method of lubricating a 2-stroke or 4-stroke marine diesel internal combustion engine comprising supplying to the internal combustion engine a lubricating composition disclosed herein. The lubricating composition is typically used to lubricate the 2-stroke marine diesel cylinder liner.

The two-stroke marine diesel engine may be a 2-stroke, cross-head slow-speed compression-ignited engine usually has a speed of below 200 rpm, such as, for example, 10-200 rpm or 60-200 rpm.

The fuel of the 2-stroke marine diesel engine may contain a sulfur content of up to 5000 ppm, or up to 3000, or up to 1000 ppm of sulfur. For example the sulfur content may be 200 ppm to 5000 ppm, or 500 ppm to 4500 ppm, or 750 ppm to 2000 ppm.

The internal combustion engine may also be a heavy duty diesel internal combustion engine.

The heavy duty diesel internal combustion engine may have a "technically permissible maximum laden mass" over 3,500 kg. The engine may be a compression ignition engine or a positive ignition natural gas (NG) or LPG (liquefied petroleum gas) engine. The internal combustion engine may be a passenger car internal combustion engine. The passenger car engine may be operated on unleaded gasoline. Unleaded gasoline is well known in the art and is defined by British Standard BS EN 228:2008 (entitled "Automotive Fuels—Unleaded Petrol—Requirements and Test Methods").

The passenger car internal combustion engine may have a reference mass not exceeding 2610 kg.

The lubricating composition may be suitable for use as a cylinder lubricant irrespective of the sulfur, phosphorus or sulfated ash (ASTM D-874) content of the fuel. The sulfur content of the lubricating composition, which is particularly suited to use as an engine oil lubricant, may be 1 wt. % or less, or 0.8 wt. % or less, or 0.5 wt. % or less, or 0.3 wt. % or less. In one embodiment, the sulfur content may be in the range of 0.001 wt. % to 0.5 wt. %, or 0.01 wt. % to 0.3 wt. %. The phosphorus content may be 0.2 wt. % or less, or 0.12 wt. % or less, or 0.1 wt. % or less, or 0.085 wt. % or less, or 0.08 wt. % or less, or even 0.06 wt. % or less, 0.055 wt. % or less, or 0.05 wt. % or less. In one embodiment, the phosphorus content may be 100 ppm to 1000 ppm, or 200 ppm to 600 ppm. The total sulfated ash content may be 2 wt. % or less, or 1.5 wt. % or less, or 1.1 wt. % or less, or 1 wt. % or less, or 0.8 wt. % or less, or 0.5 wt. % or less, or 0.4 wt. % or less. In one embodiment, the sulfated ash content may be 0.05 wt. % to 0.9 wt. %, or 0.1 wt. % to 0.2 wt. % or to 0.45 wt. %.

Without intending to limit the scope of the exemplary embodiment, the following examples illustrate preparation and evaluation of example compounds.

EXAMPLES

All reactants and additives are expressed on an oil-free basis.

Example 1

Preparation of a $C_{20}$-$C_{24}$ Alkenyl Succinimide Derivative of 4-Aminophenol A mixture of N-substituted hydroxyphenyl succinimides is formed from a mixture of 4-aminophenol (186 g) and $C_{20-24}$ alkenyl succinic anhydride (800 g). The reactants are added to a round bottom flask with xylene (436 g) then the temperature set to 160° C. After 4 hours xylene is removed via vacuum distillation, leaving the reaction product. The reaction scheme may be illustrated as follows:

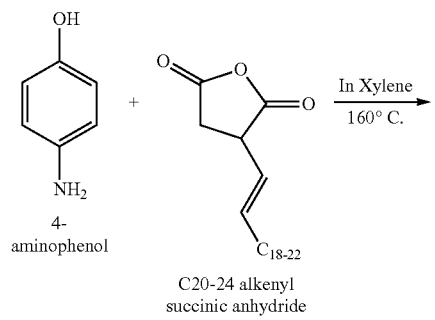

C20-24 alkenyl succinic anhydride

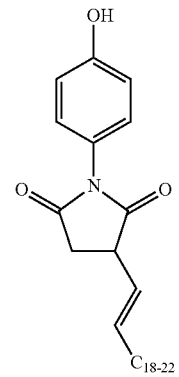

Reaction progress is monitored using FTIR and amount of water generation. NMR/ESIMS data support the expected product formation.

Example 2

Preparation of a Sulfur-Coupled $C_{20}$-$C_{24}$ Alkenyl Succinimide Derivative of 4-Aminophenol The reaction scheme is as follows:

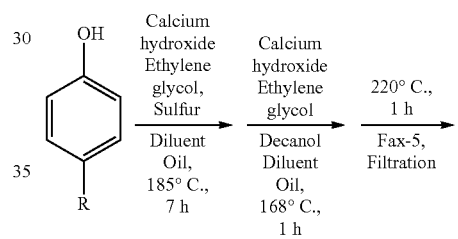

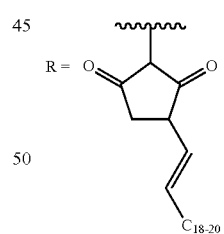

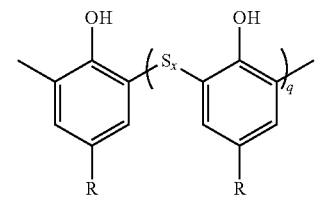

A 3 L flange flask fitted with an overhead stirrer, subsurface inlet, thermocouple, dean-stark and stopper is attached to a caustic scrubber unit. 4-alkylsuccinimide phenol (400 g) (Example 1) is added and the vessel heated to 100° C. at 400 rpm under 1 cfh nitrogen. Ethylene glycol (8.96 g) and calcium hydroxide (24.02 g) are added and the mixture heated to 124° C., followed by the addition of sulfur (43.04 g) and a further temperature increase to 185° C. The reaction mixture is held at this temperature for 7 hours before diluent oil (198.43 g) is added and the temperature is reduced to 100° C. Then, decanol (55.60 g), ethylene glycol (44.96 g) and calcium hydroxide (10.82 g) are added and the reaction heated to 168° C. and held for 1 hour. Diluent oil (691.63 g)

is added and the reaction distilled at 220° C. for 1 hour under 1 cfh nitrogen, and 30 minutes under full vacuum. The reaction is cooled to 150° C. and diatomaceous earth (10 g) added and stirred for 15 minutes. The reaction mixture is then filtered through a pad of diatomaceous earth to yield the product as a dark oil (1185.23 g, 89% yield; 1.4% Calcium; TBN=41 mg KOH/g).

Example 3

Preparation of a Methylene-Coupled $C_{20}$-$C_{24}$ Alkenyl Succinimide Derivative of 4-Aminophenol The reaction scheme is as follows:

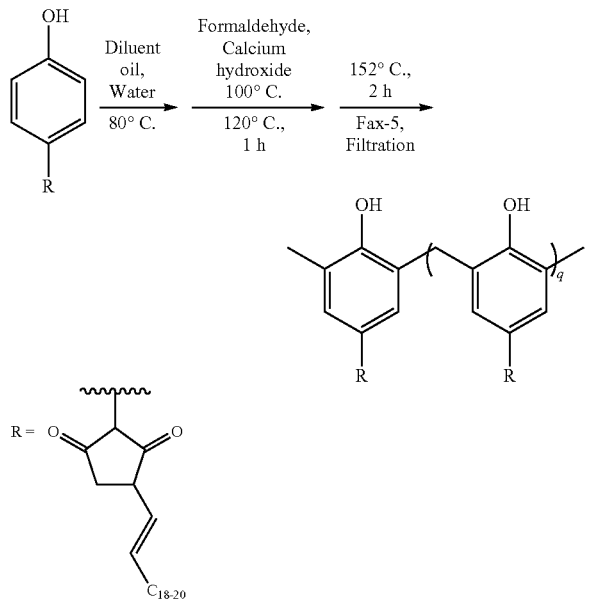

A 2 L flange flask is fitted with an overhead stirrer, subsurface inlet, thermocouple, dean-stark and stopper. 4-alkylsuccinimide phenol (400 g) (Example 1), diluent oil (754.46 g), water (20.80 g) and silicon antifoam (3 drops) are added and the mixture stirred at 400 rpm under 1 cfh nitrogen for 15 minutes followed by addition of formaldehyde (38.54 g, solid, not aqueous). Calcium hydroxide (1.36 g) is added and the reaction heated to 80° C., followed by a further charge of calcium hydroxide (26.13 g) and an increase in temperature to 100° C. The reaction mixture is then heated to 120° C. and held for 1 hour before being distilled at 152° C. for a further 2 hours. The reaction is cooled to 120° C., and diatomaceous earth (10 g) added and filtered through a pad of diatomaceous earth to yield the product as a brown oil (1128.32 g, 86%; 0.70% Calcium; TBN=20 mg KOH/g).

Example 4

Formulation of Lubricating Composition and Performance Testing

The 4 aminophenol based hydroxyphenyl succinimide substrate of Example 1 is blended into a marine diesel formulation in the place of neutral calcium sulfur-coupled phenate at equal substrate level (Table 2) and tested for key deposit control and antioxidancy.

For comparison a Baseline formulation is prepared using similar base oil.

TABLE 2

Exemplary and Baseline Formulations[1]

| Additive | Formulations (wt. %) | |
|---|---|---|
| | A. With 4-aminophenol based hydroxyphenyl succinimide | B. Baseline |
| Process oil[2] | Balance to 100% | |
| 600N Base oil | 51 | 50 |
| 150 Bright Stock | 30 | 29 |
| 400TBN Overbased Calcium Sulfonate | 9.1 | 9.1 |
| Borated PIBsuccinimide dispersant (2.8% B; 90 TBN) | 0.67 | 0.67 |
| Neutral PDDP-derived phenate detergent | 0 | 3.65 |
| Example 1 | 2.75 | |
| Anti-foam | 0.006 | 0.006 |

[1]All amounts expressed on an oil free basis
[2]Components deliver various amounts of diluent oil The baseline composition B and exemplary composition A are tested in a panel coker apparatus. 210 g of lubricating composition to be analyzed is placed in a steel sump chamber at 105° C. An agitator including several metal tongs on a spindle is inserted into the sump and spun at 1000 rpm. The apparatus is capped with a flat aluminum plate with a constant surface temperature of 325° C. The agitator sprays a continuous thin layer of oil onto the aluminum plate for a period of 4 hours. At the end of test, the plate is removed and optically rated. A rating scale is applied with 0 meaning a plate completely covered in black deposits and 100 meaning a plate completely free of deposits.

The 4-aminophenol based substrate example showed a performance boost over the baseline formulation, giving a Unit rating of 59% compared to the baseline of 46%.

As used herein, the term "comprising" is inclusive and does not exclude additional, un-recited elements or method steps. However, in each recitation of "comprising" herein, it is intended that the term also encompasses, as alternative embodiments, the phrases "consisting essentially of" and "consisting of," where "consisting of" excludes any element or steps not specified and "consisting essentially of" permits the inclusion of additional un-recited elements or steps that do not materially affect the basic and novel, and essential characteristics of the composition or method under consideration.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A lubricating composition comprising:
   an oil of lubricating viscosity; and
   an N-substituted hydroxyaromatic succinimide or a bridged compound and/or a salt thereof represented by the formula:

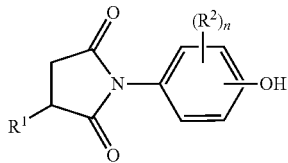

where $R^1$ is selected from the group consisting of amino groups and alkylene amine groups of the form $-(CH_2)_m NR^3R^4$, wherein $R^3$ and $R^4$ are independently selected from hydrogen and hydrocarbyl groups, and wherein at least one of $R^3$ and $R^4$ is a hydrocarbyl group of at least 8 carbon atoms;
$R^2$ is a hydrocarbyl group;
m is at least 0; and
n is 0-2.

2. The composition of claim 1, wherein n is 0.
3. The composition of claim 1, wherein m is 0.
4. The composition of claim 1, wherein the succinimide derivative of the hydroxy aromatic amine is a bridged compound represented by the formula:

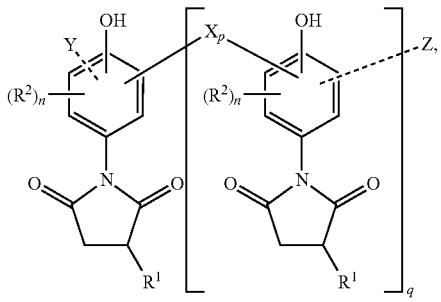

or a salt thereof,
where X is a sulfur or an alkylene link,
   X represents a bridging group,
   Y and Z each represent a terminal group,
   p is at least 1, and
   q is at least 1.

5. The lubricating composition of claim 4, wherein the compound is a metal salt or pnictogen salt.

6. The lubricating composition of claim 5, wherein the compound is a metal salt which includes at least one metal ion selected from $Li^+$, $Na^+$, $K^+$, $Rb^+$, $Cs^+$, $Be^{2+}$, $Mg^{2+}$, $Ca^{2+}$, $Sr^{2+}$ $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{4+}$, $V^{3+}$, $V^{2+}$, $Nb^{4+}$, $Nb^{3+}$, $Nb^{2+}$, $Ta^{4+}$, $Ta^{3+}$, $Ta^{2+}$, $Cr^{4+}$, $Cr^{3+}$, $Cr^{2+}$, $Cr^+$, $Mo^{4+}$, $Mo^{3+}$, $Mo^{2+}$, $Mo^+$, $W^{4+}$, $W^{3+}$, $W^{2+}$, $W^+$, $Mn^{4+}$, $Mn^{3+}$, $Mn^{2+}$, $Mn^+$, $Re^{4+}$, $Re^{3+}$, $Re^{2+}$, $Re^+$, $Fe^{6+}$, $Fe^{4+}$, $Fe^{3+}$, $Fe^{2+}$, $Fe^+$, $Ru^{4+}$, $Ru^{3+}$, $Ru^{2+}$, $Os^{4+}$, $Os^{3+}$, $Os^{2+}$, $Os^+$, $Co^{5+}$, $Co^{4+}$, $Co^{3+}$, $Co^{2+}$, $Co^+$, $Rh^{4+}$, $Ru^{3+}$, $Rh^{2+}$, $Rh^+$, $Ir^{4+}$, $Ir^{3+}$, $Ir^{2+}$, $Ir^+$, $Ni^{3+}$, $Ni^{2+}$, $Ni^{3O}$, $Pd^{4+}$, $Pd^{2+}$, $Pd^{3O}$, $Pt^{4+}$, $Pt^{3+}$, $Pt^{2+}$, $Pt^+$, $Cu^{4+}$, $Cu^{3+}$, $Cu^{2+}$, $Cu^{3O}$, $Ag^{3+}$, $Ag^{2+}$, $Ag^+$, $Au^{4+}$, $Au^{3+}$, $Au^{2+}$, $Au^+$, $Zn^{2+}$, $Zn^{3O}$, $Cd^{2+}$, $Cd^{3O}$, $Hg^{4+}$, $Hg^{2+}$, $Hg^{3O}$, $Al^{3+}$, $Al^{2+}$, $Al^{3O}$, $Ga^{3+}$, $Ga^{3O}$, $In^{3+}$, $In^{2+}$, $Tl^{3+}$, $Tl^{3O}$, $Si^{4+}$, $Si^{3+}$, $Si^{2+}$, $Si^{3O}$, $Ge^{4+}$, $Ge^{3+}$, $Ge^{2+}$, $Ge^{3O}$, $Sn^{4+}$, $Sn^{2+}$, $Pb^{4+}$, $Pb^{2+}$, $AS^{3+}$, $AS^{2+}$, $As^{3O}$, $Sb^{3+}$, $Bi^{3+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^{3O}$, $Tb^{4+}$, $Tb^{3+}$, $Tb^{2+}$, $Tb^{3O}$, $Db^{3+}$, $Db^{++}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and mixtures thereof.

7. The lubricating composition of claim 6, wherein the metal in the salt comprises calcium.

8. The lubricating composition of claim 5, wherein the metal is overbased.

9. The lubricating composition of claim 5, wherein the compound is bridged with at least one of a sulfide bridge and an alkylene bridge.

10. The composition of claim 1, wherein the hydroxyaromatic succinimide and/or salt thereof is at least 0.1 wt. % of the lubricating composition.

11. The composition of claim 10, wherein the hydroxyaromatic succinimide and/or salt thereof is present in the lubricating composition from an amount of 0.2 wt. % to 8 wt %.

12. The composition of claim 1, further comprising at least one of the group consisting of detergents, antioxidants, dispersants, antiwear agents, and friction modifiers.

13. The composition of claim 1, wherein the composition is substantially free of overbased metal-containing detergents other than the hydroxyaromatic succinimide and/or salt thereof.

14. A method of lubricating a mechanical device comprising supplying to the device the lubricating composition of claim 1.

15. The method of claim 14, wherein the mechanical device comprises an engine or driveline device.

16. The method of claim 14, wherein the mechanical device comprises a heavy duty diesel engine or a machine diesel engine.

17. A method of forming the lubricating composition of claim 1 comprising:
   reacting a hydroxyaromatic amine with a succinic anhydride which includes a hydrocarbyl group of at least 8 carbon atoms;
   bridging the reaction product of the hydroxyaromatic amine with the succinic anhydride; and
   combining a product of the reaction with an oil of lubricating viscosity.

18. The method of claim 17, further comprising forming a salt of the bridged reaction product of the hydroxyaromatic amine with the succinic anhydride.

19. The method of claim 17, further comprising overbasing the salt of the bridged reaction product of the hydroxyaromatic amine with the succinic anhydride.

* * * * *